(12) United States Patent
Eweje et al.

(10) Patent No.: US 11,679,217 B2
(45) Date of Patent: Jun. 20, 2023

(54) SYSTEMS, DEVICES, AND METHODS FOR DETERMINING A DEGREE OF RESPIRATORY EFFORT EXERTED BY A PATIENT WHILE BREATHING AND/OR DETERMINING A RESPIRATORY EFFORT SCORE FOR A PATIENT

(71) Applicant: DISATI MEDICAL, INC., Boston, MA (US)

(72) Inventors: Feyisope Eweje, Boston, MA (US); Ryan Carroll, Boston, MA (US); Aaron Rose, Chicago, IL (US); Noa Ghersin Wyrobnik, Boston, MA (US); Zoe Jewell Wolszon, Boston, MA (US)

(73) Assignee: DISATI MEDICAL, INC., Boston, MA (US)

( * ) Notice: Subject to any disclaimer, the term of this patent is extended or adjusted under 35 U.S.C. 154(b) by 0 days.

(21) Appl. No.: 17/752,834

(22) Filed: May 24, 2022

(65) Prior Publication Data
US 2022/0288333 A1 Sep. 15, 2022

Related U.S. Application Data

(63) Continuation of application No. PCT/US2020/063458, filed on Dec. 4, 2020.
(Continued)

(51) Int. Cl.
*A61M 16/00* (2006.01)
*A61B 5/08* (2006.01)

(52) U.S. Cl.
CPC ............ *A61M 16/024* (2017.08); *A61B 5/08* (2013.01); *A61M 2205/332* (2013.01); *A61M 2205/3327* (2013.01); *A61M 2230/42* (2013.01)

(58) Field of Classification Search
CPC .............. A61M 16/024; A61M 16/026; A61M 16/022; A61B 5/0535; A61B 5/0816;
(Continued)

(56) References Cited

U.S. PATENT DOCUMENTS 6,267,730 B1 7/2001 Pacunas
6,491,647 B1 12/2002 Bridger et al.
(Continued)

OTHER PUBLICATIONS

Chu, et al.; Respiration rate and volume measurements using wearable strain sensors, Scripps Research Translational Institute, Nature Partner Journals, www.nature.com/npjdigitalmed, Feb. 13, 2019; 9pp.
(Continued)

*Primary Examiner* — Joseph D. Boecker
*Assistant Examiner* — Brian T Khong
(74) *Attorney, Agent, or Firm* — Resonance IP Law, PC

(57) ABSTRACT

The present invention is a respiratory monitoring device which uses 2+ sensors to map respiratory motion in patients to interpret into a respiratory effort and severity score. The core components of the invention are contact-based sensors that measure relative motion of the chest, abdomen, and/or other key anatomical features, a processing unit which takes in the data from all sensors, an algorithm that analyzes and compares the data from each sensor to understand relative motion and interpret it into clinically-relevant information, and a display screen that shares this information with clinicians. The sensors are connected to each other and the information processing unit which shares data with the screen for display of a respiratory severity score based on analysis of Thoraco-Abdominal Asynchrony (TAA) or similar indicators of respiratory effort as measured by the sensor network and analyzed by the algorithm.

20 Claims, 18 Drawing Sheets

Related U.S. Application Data

(60) Provisional application No. 63/094,056, filed on Oct. 20, 2020, provisional application No. 62/944,355, filed on Dec. 5, 2019.

(58) Field of Classification Search
CPC ....... A61B 5/0809; A61B 5/08; A61B 5/1135; A61B 5/6823; A61B 5/683; A61B 5/6832
See application file for complete search history.

(56) References Cited

U.S. PATENT DOCUMENTS

| | | | |
|---|---|---|---|
| 6,840,907 | B1 | 1/2005 | Brydon |
| 7,267,652 | B2 | 9/2007 | Coyle et al. |
| 7,314,451 | B2 | 1/2008 | Halperin et al. |
| 7,344,498 | B1 | 3/2008 | Doughty et al. |
| 7,678,061 | B2 | 3/2010 | Lee et al. |
| 8,454,528 | B2 | 6/2013 | Yuen et al. |
| 8,992,434 | B2 | 3/2015 | Halperin et al. |
| 9,095,307 | B2 | 8/2015 | Parfenova et al. |
| 9,675,282 | B2 | 6/2017 | Morren |
| 9,750,463 | B2 | 9/2017 | Swamy et al. |
| 10,052,048 | B2 | 8/2018 | Klewer et al. |
| 10,159,421 | B2 | 12/2018 | Heneghan |
| 10,869,619 | B2 | 12/2020 | Hoskuldsson et al. |
| 11,051,714 | B2 | 7/2021 | Aliverti et al. |
| 11,055,575 | B2 | 7/2021 | Anushiravani et al. |
| 2003/0139691 | A1* | 7/2003 | Kumar .............. A61B 5/6805 600/587 |
| 2005/0113673 | A1* | 5/2005 | Avinash ............. A61B 6/541 600/509 |
| 2011/0060215 | A1 | 3/2011 | Tupin, Jr. et al. |
| 2014/0276173 | A1 | 9/2014 | Banner et al. |
| 2016/0029949 | A1* | 2/2016 | Landesberg ......... A61B 5/7278 600/534 |
| 2017/0209074 | A1 | 7/2017 | Siu et al. |
| 2018/0098739 | A1 | 4/2018 | Freeman et al. |
| 2018/0129786 | A1 | 5/2018 | Khine et al. |
| 2018/0280646 | A1* | 10/2018 | Freeman ............. A61M 16/024 |

OTHER PUBLICATIONS

Matlock, et al.; Work of Breathing in Premature Neonates: Noninvasive Neurally-Adjusted Ventilatory Assist versus Noninvasive Ventilation; Respiratory Care Paper in Press. Published on Feb. 18, 2020 as DOI: 10.4187/respcare.07257; 8 pp.
Disati Medical, Inc.; International Application No. PCT/US2020/063458 filed Dec. 4, 2020; International Search Report and Written Opinion; ISA/US; dated Apr. 8, 2021; 12 pp.
Akoumianaki, Evangelia et al.; The Application of Esophageal Pressure Measurement in Patients With Respiratory Failure; American Journal of Respiratory and Critical Care Medicine vol. 189 No. 5 | Mar. 1, 2014; 12 pp.
Antony, Raj A. et al.; Clinical Validation of a Wearable Respiratory Rate Device for Neonatal Monitoring; IEEE; 2018; 4pp.
Banner, Michael J et al.; Noninvasive Work of Breathing Improves Prediction of Post-Extubation Outcome; Intensive Care Med (2012) 38:248-255.
Banner, Michael J. et al.; Power of Breathing Determined Noninvasively With Use of Anartificial Neural Network in Patients With Respiratory Failure*; Crit Care Med 2006 vol. 34, No. 4; 8 pp.
Bellani, Giacomo et al.; Assessing Effort and Work of Breathing; Curr Opin Crit Care 2014, 20:352-358.
Bernardi, Eva e tal; Respiratory Muscle Training With Normocapnic Hyperpnea Improves Ventilatory Pattern and Thoracoabdominal Coordination, and Reduces Oxygen Desaturation During Endurance Exercise Testing in COPD Patients; International Journal of COPD; Sep. 10, 2015; 8 pp.
Brennan, Colleen et al.; Thoracoabdominal Asynchrony is Not Associated With Oxyhemoglobin Saturation in Recovering Premature Infants; Neonatology 2017;111:297-302; Dec. 24, 2016.
Brochard, Laurent et al.; Clinical Review: Respiratory Monitoring in the ICU—A Consensus of 16; Brochard et al. Critical Care 2012, 16:219; http://ccforum.com/content/16/2/219; 14 pp.
Charles; Elinor et al.; Work of Breathing During HHHFNC and Synchronised NIPPV Following Extubation; European Journal of Pediatrics; https://doi.org/10.1007/s00431-018-3254-3; Oct. 30, 2018; 6 pp.
Chu, Michael et al.; Respiration Rate and Volumn Measurements Using Wearable Strain Sensors; npj Digital Medicine (2019) 2:8 ; https://doi.org/10.1038/s41746-019-0083-3; 9 pp.
Cohen, Carol A. et al.; Clinical Manifestations of Lnspiratory Muscle Fatigue; The American Journal of Medicine; vol. 73; Sep. 1982; 9 pp.
Da Silvia Junior, Everet Pereira et al; A Telemedicine Instrument for Internet-Based Home Monitoring of Thoracoabdominal Motion in Patients With Respiratory Diseases; Rev. Sci. Instrum. 82, 014301 (2011); https://doi.org/10.1063/1.3529443; Jan. 27, 2011; 10 pp.
Dadlez, Nina M. et al.; Risk Factors for Respiratory Decompensation Among Healthy Infants With Bronchiolitis; The American Academy of Pediatrics; https://doi.org/10.1542/hpeds.2017-0034; 2017; 6 pp.
De Groot, Marcel G. et al.; Interobserver Agreement on Clinical Judgment of Work of Breathing in Spontaneously Breathing Children in the Pediatric Intensive Care Unit; J Pediatr Intensive Care 2020;9:34-39.
De Groote, A et al.; Chest Wall Motion During Tidal Breathing; The American Physiological Society; 1997; 7 pp.
Dellaca, Raffaele L. et al.; Measurement of Total and Compartmental Lung Volume Changes in Newborns by Optoelectronic Plethysmography; Pediatric Research; vol. 67, No. 1; 2010; 6 pp.
Doheny, Emer P. et al.; Estimation of Respiration Rate and Sleeping Position Using a Wearable Accelerometer; IEEE; 978-1-7281-1990-8/20; 4 pp.
Drummond, Gordon B.; Classifying Signals From a Wearable Accelerometer Device to Measure Respiratory Rate; ERJ Open Res 2021; 7: 00681-2020 [https://doi.org/10.1183/23120541.00681-2020; 9 pp.
Fitting, J.W.; Clinical Significance of Abnormal Rib Cage-Abdominal Motion; Eur Resp J; 1988; 1, 498-497.
Hammer, J. et al.; Assessment of Thoraco-Abdominal Asynchrony; Elsevier; Paediatric Respiratory Reviews 10 (2009) 75-80.
Jin, Anmin et al.; Performance Evaluation of a Tri-Axial Accelerometry-Based Respiration Monitoring for Ambient Assisted Living; 31st Annual International Conference of the IEEE EMBS; Minneapolis, Minnesota, USA, Sep. 2-6, 2009; 4 pp.
Karlsson, Carl Mathias et al.; Acute Respiratory Compromise in the Emergency Department: A Description and Analysis of 3571 Events From the Get With the Guidelines-Resuscitation® Registry; HHS Public Access; Author Manuscript; J. Emerg. Med.; Apr. 2017; 52(4): 393-402.
Kashevnik, Alexey et al.; Estimation of Motion and Respiratory Characteristics During the Meditation Practice Based on Video Analysis; Sensors 2021, 21, 3771. https://doi.org/10.3390/s21113771; 22 pp.
Keneko, Hideo; Estimating Breathing Movements of the Chest and Abdominal Wall Using a Simple, Newly Developed Breathing Movement-Measuring Device; Respiratory Care; Jul. 2014; vol. 59; No. 7; 7 pp.
Kohn, S. et al.; Monitoring the Respiratory Rate By Miniature Motion Sensors in Premature Infants: A Comparative Study; Journal of Perinatology (2016) 36, 116-120.
Landesberg, Amir et al.; A New Method for Continuous Monitoring of Chest Wall Movement to Characterize Hypoxemic Episodes During HFOV; Intensive Care Med (2011) 37:1174-1181.
Liu, Guan-Zheng et al.; Estimation of Respiration Rate From Three-Dimensional Acceleration Data Based on Body Sensor Network; Telemedicine and e-Health; Mary Ann Liebert, Inc.; vol. 17; No. Nov. 9, 2011; 7 pp.
Lomauro, Antonella et al.; Can Breathing Pattern Assessment Predict the Need of Ventilatory Support in Treated SMA1 Infants?; The American Thoracic Society; Apr. 15, 2022; 10 pp.

(56) References Cited

OTHER PUBLICATIONS

Mannini, Andrea et al.; Machine Learning Methods for Classifying Human Physical Activity From On-Body Accelerometers; Sensors 2010, 10, 1154-1175; doi:10.3390/s100201154.
Midulla, Fabio et al.; The Breathless Infants; Rome Italy; accessed 2022; 4 pp.
Mimoz, O. et al.; Accuracy of Respiratory Rate Monitoring Using a Non-Invasive Acoustic Method After General Anaesthesia; British Journal of Anaesthesia 108 (5): 872-5 (2012); Advance Access publication Feb. 8, 2012; 4 pp.
Munoz, Isabel Cristina et al.; Estimation of Work of Breathing From Respiratory Muscle Activity in Spontaneous Ventilation: A Pilot Study; Appl. Sci. 2019, 9, 2007; doi:10.3390/app9102007; 18 pp.
Newth, Christopher; Measurements of Thoracoabdominal Asynchrony and Work of Breathing in Children; https://www.researchgate.net/publication/254194325; Jan. 2005; 10 pp.
Ni, Xiaoyue et al.; Automated, Multiparametric Monitoring of Respiratory Biomarkers and Vital Signs in Clinical and Home Settings for COVID-19 Patients; PNAS 2021 vol. 118 No. 19 e2026610118; 12 pp.
Phan, D.H et al.; Estimation of Respiratory Waveform and Heart Rate Using an Accelerometer; 30th Annual International IEEE EMBS Conference; Vancouver, British Columbia, Canada, Aug. 20-24, 2008; 4pp.
Ratnagiri, Madhavi V. et al.; Machine Learning for Automatic Identification of Thoracoabdominal Asynchrony in Children; International Pediatric Research Foundation, Inc.; Jul. 3, 2020; 7 pp.
Roussos, C. et al; Fatigue of Inspiratory Muscles and Their Synergic Behavior; The American Physiological Society; Jan. 22, 1979; 8 pp/.
Saria, Suchi et al.; Integration of Early Physiological Responses Predicts Later Illness Severity in Preterm Infants; NIH Public Access; Author Manuscript; Sci Transl Med. Sep. 8, 2010; 2(48):48ra65. doi:10.1126/scitranslmed.3001304.; 19 pp.
Sathyanarayana, Aarti et al.; Sleep Quality Prediction From Wearable Data Using DeepLearning; JMIR Mhealth Uhealth 2016; vol. 4; iss. 4; e125; 13 pp.
Shein, Steven L.; Derivation and Validation of an Objective Effort of Breathing Score in Critically Ill Children; Pediatric Critical Care Medicine; www.pccmjournal.org; 2018; 8 pp.
Shikora, Scott A. et al.; Work of Breathing: Reliable Predictor of Weaning and Extubation; Critical Care Medicine; vol. 18, No. 2; Feb. 1990; 6 pp.
Suresh, Harini et al.; Clinical Intervention Prediction and Understanding Using Deep Networks; Clinical Event Prediction and Understanding Using Deep Networks; May 23, 2017; 16 pp.
Tobin, Martin J,; et al.; Does Rib Cage-Abdominal Paradox Signify Respiratiory Muscle Fatigue? The American Physiological Society; 1987; 10 pp.
Tonelli, Robert et al; Early Inspiratory Effort Assessment by Esophageal Manometry Predicts Noninvasive Ventilation Outcome in De Novo Respiratory Failure: A Pilot Study; American Journal of Respiratory and Critical Care Medicine; vol. 202; No. 4; Aug. 15, 2020; 10 pp.
Tulaimat, Aiman et al.; Diaphragm: A Mnemonic to Describe the Work of Breathing in Patients With Respiratory Failure; PLoS One 12(7): e0179641. https://doi.org/10.1371/journal; pone.0179641; 12 pp, Publishing Date: Jul. 3, 2017.
Tulaimat, Aiman et al.; Association Between Rating of Respiratory Distress and Vital Signs, Severity of Illness, Intubation, and Mortality in Acutely Ill Subjects; Respiratory Care ; Sep. 2014; vol. 59; No. 9; 7 pp.
Van Loon, Kim et al.; Non-Invasive Continuous Respiratory Monitoring on General Hospital Wards: A Systematic Review; Plos One | DOI:10.1371/journal.pone.0144626 Dec. 14, 2015; 14 pp.
Waisman, Dan et al.; Real-Time Detection, Classification, and Quantification of Apneic Episodes Using Miniature Surface Motion Sensors in Rats; International Pediatric Research Foundation, Inc.; vol. 78; No. 1; Jul. 2015; 8 pp.
Wang, Wenjin et al.; Physiol. Meas.; Algorithmic Insights of Camera-Based Respiratory Motion Extraction; in press https://doi.org/10.1088/1361-6579/ac5b49; 2022; 31 pp.
Witt, Whitney P.; et al.; Overview of Hospital Stays for Children in the United States, 2012; Healthcare Cost and Utilization Project; Agency for Healthcare Research and Quality; Dec. 2014; 17 pp.

* cited by examiner

| Product | Function | Limitations |
|---|---|---|
| Philips ChARM | Originally created with the aim of aiding pneumonia diagnosis in low-resource settings; company is currently working on a next-generation version with pulse oximetry and temperature sensing | Sensitivity to movement artifacts, inability to provide any volumetric information or muscular activity measurement resulting in an incomplete picture of respiratory status |
| Healthcare Originals ADAMM | Provides heart beat rate, respiratory rate, skin temperature, activity, and identification of abnormal breath sounds including coughing and wheezing | Designed to identify acute symptoms in asthmatics in the day-to-day rather than continuous monitoring of breathing effort |
| Skiin | Smart textiles for ECG, heart rate variability, stress levels, sleep quality, steps, distance, calories burned, active minutes, stationary time monitoring; also analyzes breathing patterns including deep versus shallow breaths and respiratory rate | Provides indication of breath type and respiratory rate but does not tie this information to breathing effort |
| Resperate by LifeMatters | Provides information on coordination of the breathing and the heart rate variability with the goal of reducing blood pressure | Target use case focused on lowering blood pressure; does not tie analyzed data to breathing effort |
| BreathResearch | Auditory monitoring of breath sounds with an eye towards detecting breathing difficulty or respiratory disease | Designed primarily non-clinical use for highperformance athletes or those seeking to optimize their breathing patterns |
| Macawi Dipha+ | Enables users to assess activity of the diaphragm and intercostal muscles using surface EMG; used in pulmonological research with a focus on the muscle use during breathing | Not made available for clinical or commercial use |

SYSTEMS, DEVICES, AND METHODS FOR DETERMINING A DEGREE OF RESPIRATORY EFFORT EXERTED BY A PATIENT WHILE BREATHING AND/OR DETERMINING A RESPIRATORY EFFORT SCORE FOR A PATIENT

RELATED APPLICATIONS

The present application is a CONTINUATION of International Application Number PCT/US2020/063458, filed Dec. 4, 2020, which is an INTERNATIONAL APPLICATION (PCT) of U.S. Provisional Patent Application No. 62/944,355, filed on 5 Dec. 2019 and entitled "RESPIRATORY SEVERITY ASSESSMENT USING MOTION-BASED SENSING" and U.S. Provisional Patent Application No. 63/094,056, filed on 20 Oct. 2020 and entitled "SYSTEMS, DEVICES, AND METHODS FOR THORACOABDOMINAL ASYNCHRONY-BASED RESPIRATORY EFFORT ASSESSMENT IN PATIENTS," both of which are incorporated, in their entireties, herein.

BACKGROUND

Respiratory diseases are a major global cause of morbidity and mortality in children and adults. These illnesses include Respiratory Distress Syndrome (RDS), Acute Respiratory Distress Syndrome (ARDS), Pediatric Acute Respiratory Distress Syndrome (PARDS), asthma, and upper and lower respiratory tract infections, such as croup, bronchiolitis and pneumonia. Among pediatric intensive care unit (PICU) patients not admitted for respiratory illness, respiratory distress is of great concern because unrecognized respiratory failure is the leading cause of cardiopulmonary arrest in infants; and respiratory arrest is a major contributor to adult mortality. Early recognition and treatment are critical to reducing morbidity and mortality. Thus, respiratory monitoring to ensure appropriate utilization of respiratory support is a critical area of focus for general and ICU clinicians.

Traditionally, respiratory effort exerted by patients has been assessed using both direct and indirect methods. The most direct assessment of respiratory effort is the calculation of work of breathing, or overall energy expenditure associated with respiration, which may be calculated as the integral of the product of respiratory volume and pressure. Esophageal manometry, defined as pressure measured by a balloon catheter placed in a patient's esophagus, is considered a gold standard for minimally invasive, quantitative assessment of respiratory effort through work of breathing calculation; however, it is not widely adopted in clinical practice due to poor interpretability by clinicians.

Less direct approaches to measure work of breathing rely on assessing conditions such as labored breathing or respiratory distress, or dyspnea, while the patient is at rest, the patient's use of accessory respiratory muscles, and measuring paradoxical motion of the patient's abdomen in qualitative or semiquantitative ways. One example of an existing clinical standard for objective clinical assessment of respiratory distress in children and infants known as the Silverman Andersen respiratory severity score (RSS). The RSS is a semiquantitative assessment of five parameters correlated with work of breathing that has been pioneered for use in low-resource settings. RSS scores range from 0 to 10 based on the summed severity grades of five parameters said to be at grade 0, 1, or 2. However, as with many clinical assessment guidelines, this metric suffers from poor interobserver variability which may only be rectified by continuous, extensive training for the retention of assessment skills. In addition, this assessment relies on the availability and direct observation of medical professionals and does not allow for continuous monitoring, potentially compromising the ability to detect increased breathing effort at its onset and intervene in a timely manner.

FIG. 1 provides a table of tools currently available that indirectly assess a degree of effort a patient exerts to breathe via mechanical, acoustic, and/or electrical sensing devices along with a description of their respective functions and limitations. While each of these tools has the ability to measure one or multiple signatures of breathing effort, each has unique limitations related to accuracy, ability to tie monitored data to breathing effort, and commercial availability that limit their respective usefulness and accuracy, particularly in a clinical setting.

BRIEF DESCRIPTION OF THE DRAWINGS

FIG. 1 provides a table of tools currently available that indirectly assess a degree of effort a patient exerts to breathe via mechanical, acoustic, and/or electrical sensing devices along with a description of their respective functions and limitations, in accordance with embodiments of the present invention;

SUMMARY

Figure 2A:
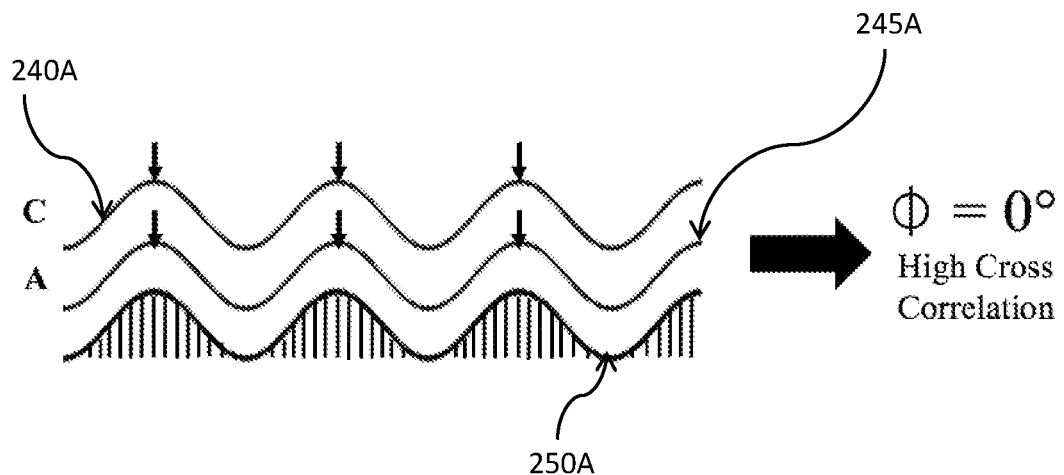
FIG. 2A provides a graph that shows a first chest signal aligned in time with a first abdominal signal, in accordance with embodiments of the present invention.

Systems for monitoring a patient's respiratory system may include a first sensor communicatively coupled to a processor and configured to be positioned on a patient's chest and capture a movement of the patient's chest, a second sensor communicatively coupled to a processor and configured to be positioned proximate to the patient's xiphoid process and capture a movement of the patient's xiphoid process, a third sensor communicatively coupled to a processor and configured to be positioned on a patient's abdomen and capture a movement of the patient's abdomen, and a power source for providing electrical power to the first, second, and third sensors. The first, second, and/or third sensors may be, for example, accelerometers, force sensors and/or strain gauges.

In some embodiments, the system also includes a controller communicatively coupled to at least one of the first, second, and third sensors and the processor. The controller may be configured to, for example, extract movement measurements, acceleration measurements, force measurements, strain measurements, respiratory rate, and/or a degree of thoraco-abdominal asynchrony (TAA) exhibited by the patient and communicate the extracted movement measurements, acceleration measurements, force measurements, strain measurements, respiratory rate, and/or degree of TAA to the processor.

Additionally, or alternatively, the system may include a first wire mechanically and electrically coupling the first and second sensors together and a second wire mechanically and electrically coupling the second and third sensors together. In some instances, a length of the first wire and/or the second wire may be adjustable via, for example, a retractable spool or when an expandable wire may be used.

In some embodiments, the processor of the system may be in communication with a memory with a set of instructions stored thereon, which when executed by the processor cause the processor to perform a number of steps such as receiving a first set of sensor data from a first sensor positioned on the epidermis of a patient in a first location, receive a second set of sensor data from a second sensor positioned on the epidermis of the patient in a second location, determine a phase difference between the first and second sets of sensor data and/or perform a cross-correlation analysis on the first and second sets of sensor data, determine a degree of respiratory effort exhibited by the patient based on a determined phase difference between the first and second sets of sensor data and/or a result of the cross-correlation analysis and communicate the degree of respiratory effort to a display device. In some embodiments, the processor of the system may also receive a third set of sensor data from the third sensor positioned on the epidermis of the patient in a third location, the third sensor being in communication with the processor, determine a phase difference between at least one of the first and third sets of sensor data and/or the second and third sets of sensor data and/or perform a cross-correlation analysis on the first and third sets of sensor data and/or the second and third sets of sensor data, and determine a degree of respiratory effort exhibited by the patient based on a determined phase difference between the first and third sets of sensor data and/or the second and third sets of sensor data and/or based on a result of the cross-correlation analysis.

Exemplary methods performed by a processor when using the invention include receiving a first set of sensor data from a first sensor positioned on the epidermis of a patient in a first location, receiving a second set of sensor data from a second sensor positioned on the epidermis of the patient in a second location, determining a phase difference between the first and second sets of sensor data, determining a degree of respiratory effort exhibited by the patient based on a determined phase difference between the first and second sets of sensor data, and communicating the degree of respiratory effort to a display device. In some embodiments, a determination of the degree of respiratory effort exhibited by the patient may include determining a degree of thoraco-abdominal asynchrony (TAA) exhibited by the patient. The first location may be the patient's chest or proximate to the patient's xiphoid process and the second location may be proximate to the patient's xiphoid process or abdomen.

At times, the first set and/or second set(s) of sensor data may be pre-processed or filtered (e.g., bandpass filtering) prior to determining the phase difference. The first and second sensors may be, for example, accelerometers and the first and second sets of sensor data include acceleration measurements. Additionally, or alternatively, the first and second sensors may be force meters and the first and second sets of sensor data include force measurements. Additionally, or alternatively, the first and second sensors may be strain sensors and the first and second sets of sensor data include strain measurements.

In some embodiments, an indication of a respiratory rate of the patient may be received and the determination of the degree of respiratory effort exhibited by the patient may be further based on the respiratory rate.

In some embodiments, a third set of sensor data may be received from a third sensor positioned on the patient in a third location. A phase difference between first and third sets of sensor data and/or the second and third sets of sensor data may then be determined and the determination of the degree of respiratory effort exhibited by the patient may be further based on a determined phase difference between the first and third sets of sensor data and/or the second and third sets of sensor data.

In some embodiments, a cross-correlation analysis between the first and second sets of sensor data may be completed prior to determining the degree of respiratory effort exhibited by the patient, wherein the degree of respiratory effort exhibited by the patient may be further based on a result of the cross-correlation analysis.

In some embodiments, the first and second sets of sensor data may be a signal collected over a period of time and a result of a cross-correlation calculation at a particular time during the period of time may be mapped with a maximum theoretical cross-correlation value or maximum cross-correlation value calculated during the period of time prior to the determination of the degree of respiratory effort exhibited by the patient.

Additionally, or alternatively, a video recording of a patient's thorax while the patient may be breathing for a period of time may be received so that motion of the patient's thorax, or portions thereof, may be observed and/or measured. At times, motion may be relative movement of the patient's thorax while the patient may be breathing. In some embodiments, the video recording is a three-dimensional video recording. Optionally, in some cases, an epidermis of the patient's thorax may be marked with a first marker positioned on the epidermis of the patient in a first location (e.g., chest or xiphoid process) and a second marker positioned on the epidermis of the patient in a second location (e.g., xiphoid process or abdomen)—but this need not always be the case. Exemplary markers include dots or graphics drawn on the skin of the patient, stickers, LEDs, and radio-opaque markers. The video may then be analyzed to determine changes in position of the first and second markers over the period of time and a first waveform showing changes in position of the first marker over the period of time along with a second waveform showing changes in position of the second marker over the period of time may be formed or generated. In some cases, the first and/or second waveforms may be sinusoidal. A phase difference between the first and second waveforms may be determined, and a degree of respiratory effort exhibited by the patient be further determined using the determined phase difference. Additionally, or alternatively, a cross-correlation analysis may be performed using the first and second waveforms and the degree of respiratory effort exhibited by the patient be further determined using a result of the cross-correlation analysis. The degree of respiratory effort may then be communicated to a display device as, for example, a respiratory effort score, a respiratory distress severity score, or other indicator of respiratory effort. In some cases, the determination of the degree of respiratory effort exhibited by the patient may include determining a degree of thoraco-abdominal asynchrony (TAA) exhibited by the patient. Additionally, or alternatively, an indication of a respiratory rate of the patient, and the determination of the degree of respiratory effort exhibited by the patient may be further based on the respiratory rate.

In some embodiments, a cross-correlation analysis between the first and second sets of sensor data may be performed prior to determining the degree of respiratory effort exhibited by the patient, wherein the degree of respiratory effort exhibited by the patient may be further based on a result of the cross-correlation analysis. In these embodiments, the first and second sets of sensor data may be a signal collected over a period of time and a result of a cross-correlation calculation at a particular time during the period of time may be mapped with a maximum theoretical cross-correlation value or maximum cross-correlation value calculated during the period of time prior to the determination of the degree of respiratory effort exhibited by the patient.

Written Description

Management of COVID-19 associated respiratory distress must consider the full spectrum of invasive and non-invasive ventilation options because prolonged use of an ICU bed and ventilator consumes resources that may not be readily available in constrained settings. Physicians must also balance the risk of ventilator-induced lung injury and extubation challenges that come with prolonged ventilator use with the risk of poorer outcomes with inappropriately delayed intubation. The decision to intubate or offer less invasive forms of respiratory support is often complicated by the degree of variability in presentation among patients with similar levels of respiratory function. Recent guidance regarding management of COVID-19 has suggested that some patients can be offered non-invasive support such as BiPAP, CPAP or HFNC, but they must be closely monitored for signs of respiratory effort deterioration, such as signs of increased work of breathing in the presence of hypoxia, use of accessory muscles, and tachypnea.

While esophageal manometry has been acknowledged as a gold standard for deriving the work of breathing from respiratory pressures, it has shown limited clinical utility due to its invasive nature and limited interpretability of the output measurements. A clinical metric that has been suggested as a signature of breathing effort (also referred to herein as "work of breathing") is thoracoabdominal asynchrony (TAA), the non-coincident motion of the rib cage and abdomen during breathing. In a healthy patient, the chest wall and abdomen expand and retract in a synchronous manner during respiration; as the patient enters respiratory distress, asynchronous motion of the chest and abdomen becomes increasingly prominent. In its worst manifestation, the rib cage and abdomen move according to periodic functions that are 180° out of phase, a phenomenon referred to as "see-saw" breathing.

In addition to escalation guidance, having a feedback mechanism that can guide de-escalation of respiratory support will be critical in successfully and efficiently treating COVID-19 patients. Successful extubation is especially important in COVID-19 management because of the risks of aerosolization during multiple cycles of intubation-extubation. Monitoring real-time changes in TAA could play an important role in guiding ventilatory support weaning. A recently published extubation protocol for COVID-19 patients suggested observing for signs such as TAA during spontaneous breathing trials (SBT) to ensure the success of SBTs during the weaning process. Such monitoring can be especially important for high-risk patients in which weaning can be more challenging. Among these risk factors is obesity, a co-morbidity that affects up to half of adult COVID patients. Obesity can restrict ventilation by impeding diaphragm excursion, impairing immune responses to viral infection, promoting a pro-inflammatory state, and inducing oxidant stress that can adversely affect cardiovascular function. Importantly, TAA has been shown to be elevated in subjects with significant abdominal obesity, raising the risk of hypoxia ventilation-perfusion mismatching and impaired gas exchanges.

The clinical standard for TAA monitoring involves periodic visual observation by members of the respiratory care team. Such subjective assessment practices can suffer from poor interobserver variability. For COVID-19 as well as the full spectrum of acute respiratory illness, a reliable, objective assessment tool for continuous monitoring of respiratory effort could allow for a more complete understanding of patients' real-time respiratory status and provide an additional indication or contraindication for the utilization of various levels of ventilatory support.

Figure 2B:
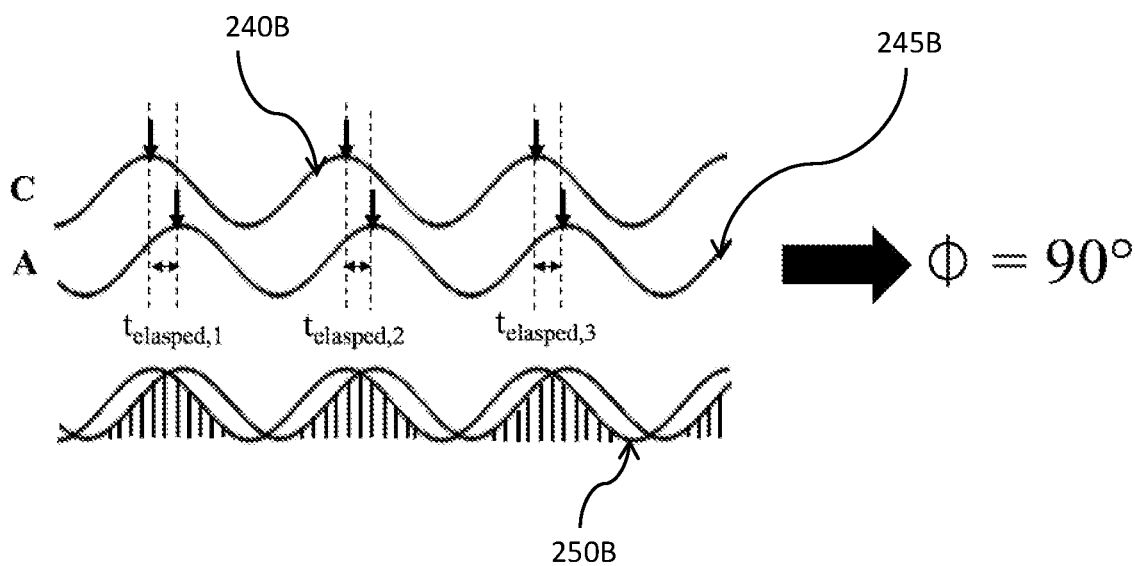
FIG. 2B provides a graph that shows a second chest signal aligned in time with a second abdominal signal, in accordance with embodiments of the present invention.
Figure 2C:
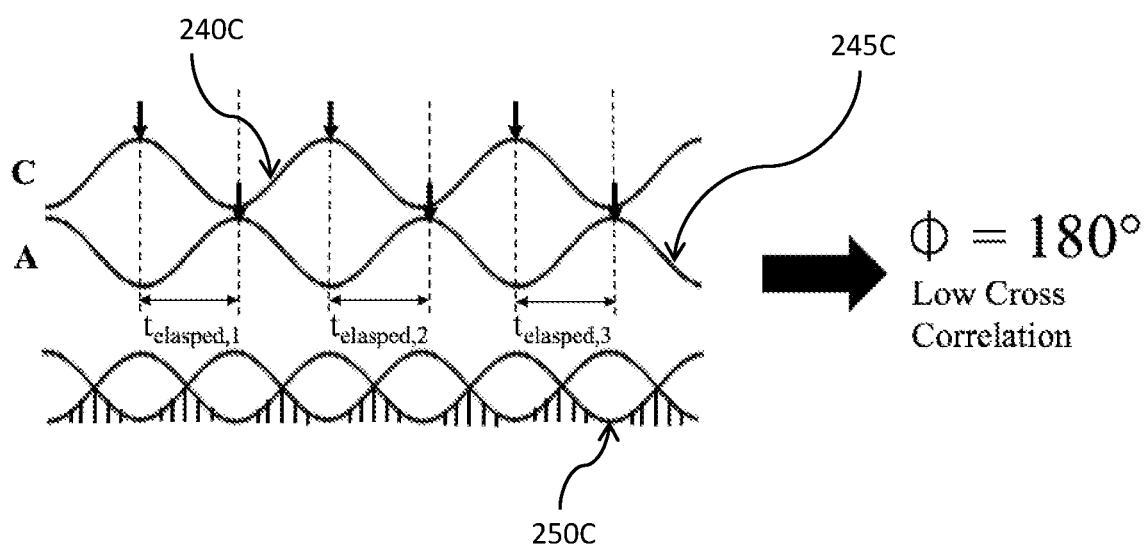
FIG. 2C provides a graph that shows a third chest signal aligned in time with a third abdominal signal, in accordance with embodiments of the present invention.

FIGS. 2A-2C provide graphs 210, 220, and 230, respectively, that show a sinusoidal signal from a sensor positioned on a patient's chest that is labeled "C" on the graphs (sometimes referred to as a "chest signal" herein), a sinusoidal signal from a sensor positioned on the patient's abdomen that is labeled "A" on the graphs (sometimes referred to as an "abdominal signal" herein), and a composite graph showing the first (chest) sinusoidal signal superimposed over the second (abdominal) signal so that, for example, a phase difference (Ø) therebetween may be observed or determined. The maximum amplitude for each oscillation of the chest and abdominal signals is marked with an arrow. In addition, the chest and abdominal sinusoidal signals are aligned in the time domain so that they correspond to one another in time (e.g., have the same start and end time and progress in time at the same rate). More specifically, FIG. 2A provides a graph 210 that shows a first chest signal 240A aligned in time with a first abdominal signal 245A. Graph 210 also provides a composite signal 250A of the first chest signal 240A super first abdominal signal 245A. First chest signal 240A is highly correlated (i.e., high cross correlation) with first abdominal signal 245A so that a phase difference (Ø) between them is approximately 0°. Because there is a high correlation between the first chest signal 240A and the first abdominal signal 245A, the patient associated with the first chest signal 240A and the first abdominal signal 245A exhibits little, to no, TAA and is demonstrating little, or normal, effort while breathing.

More specifically, FIG. 2B provides a graph 220 that shows a second chest signal 240B aligned in time with a second abdominal signal 245B. Graph 210 also provides a composite signal 250B of the second chest signal 240B super second abdominal signal 245B. Second chest signal 240B is not highly correlated (i.e., low cross correlation) with second abdominal signal 245B so that a phase difference (Ø) between them is approximately 90°. Because there is not high correlation between the second chest signal 240B and the second abdominal signal 245B, the patient associated with the second chest signal 240B and the second abdominal signal 245B exhibits some TAA, is demonstrating elevated effort while breathing, and is likely in some respiratory distress.

More specifically, FIG. 2C provides a graph 230 that shows a third chest signal 240C aligned in time with a third abdominal signal 245C. Graph 210 also provides a composite signal 250C of the third chest signal 240C super third abdominal signal 245C. Third chest signal 240C is not correlated (i.e., no cross correlation) with third abdominal signal 245C so that a phase difference (Ø) between them is approximately 180°. Because there is no correlation between the third chest signal 240C and the third abdominal signal 245C, the patient associated with the third chest signal 240C and the third abdominal signal 245C exhibits severe TAA and is likely exerting extreme effort while breathing and is likely in severe respiratory distress.

In a healthy patient, the chest wall and abdomen expand and retract in a synchronous manner during respiration, with a high cross-correlation and a phase difference of approximately 0° as shown in the first composite signal 250A of first graph 210 of FIG. 2A. As the patient enters respiratory distress, asynchronous motion between the chest and abdomen becomes increasingly prominent as may be seen in graph 220 of FIG. 2B and, more particularly, in the second composite signal 250B where a frequency of chest motion is 90° out of phase with the frequency of abdominal motion. In its worst manifestation, chest and abdominal movement become completely asynchronous, or exhibit low cross-correlation of approximately 180° out of phase with one another as may be seen in the third composite signal 250C of graph 230 of FIG. 2C. This phenomenon of asynchronous breathing (as shown in FIG. 2C) is sometimes referred to as "see-saw" breathing.

Asynchronous breathing is a symptom of respiratory distress for all types of patients regardless of, for example, age, size, body mass index, waist size, chest size, and/or gender. However, in some cases, a level, or degree, of asynchronous breathing may be dependent upon physiological characteristics of a patient and may not be caused by respiratory distress (e.g., a patient with a higher BMI, or larger adipose layer proximate to the abdomen may obscure extremes of movement of the abdomen or portions of the thorax and, in some cases, may not manifest as dramatic asynchrony as an individual with a lower BMI or smaller adipose layer). For example, in adult patients with a relatively large adipose tissue layer positioned on, or around, the abdomen, this adipose tissue layer may cause some compression on the diaphragm that may lead to a degree of asynchronous breathing that is not resultant from respiratory distress. However, when such a patient is, or may be, in such respiratory distress the systems and processes described herein may be able to adjust measurements and other analysis to correct for adipose tissue positioned on, or around, the abdomen.

Thus, a determination of a degree of severity for asynchronous breathing of a patient may be absolute (e.g., measured against a known baseline or set of baselines) or may be relative to a patient's breathing pattern while healthy and his or her breathing pattern while diseased state or absolute.

Figure 3A:
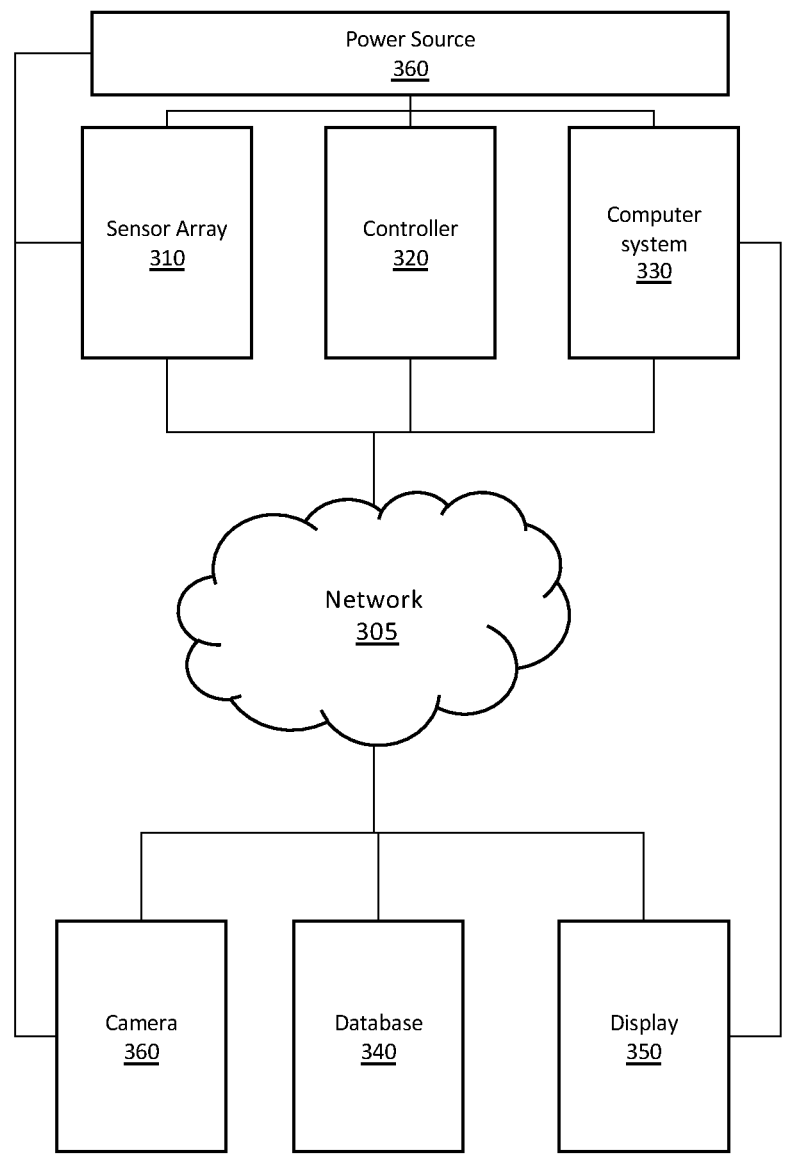
FIG. 3A presents an exemplary system that may be configured to execute one or more methods disclosed herein, in accordance with embodiments of the present invention.

FIG. 3A presents an exemplary system 300 that may be configured to execute one or more methods disclosed herein. In some cases, system 300 (or portions thereof) may gather data that may be used to assess respiratory effort of a patient and make determinations of respiratory distress (e.g., a respiratory distress score) for the patient using system 300, or portions thereof. System 300 includes a sensor array 310 configured to measure chest and abdomen motion during respiration, a controller 320 configured to received data from the sensor array 310, extract, for example, movement, TAA, and/or respiratory rate from the sensor array data and provide the extracted data to a computer system 330 that, in many cases, includes a display interface to visualize data for viewing by a user. In some embodiments, controller 320 may be a microcontroller. System 300 may also include a power source 360 that may be electrically coupled to one or more components of system 300. Power source 360 may be configured to provide electrical power to one or more components of system 300. Exemplary power sources include but are not limited to a battery and a mechanism by which to plug into a wall outlet and draw power from a main power supply.

Sensor array 310 may include a plurality (e.g., 2-10) sensors that may be configured to sense movement of a patient. Exemplary sensors included in sensor array 310 include, but are not limited to, accelerometers (e.g., 2-dimensional and/or three-dimensional accelerometers), force meters, and/or strain-based sensors (sometimes referred to as strain gauges). Exemplary accelerometers that may be included in sensor array 310 are an Invensense ICM-20602 6-axis gyroscope and/or accelerometer with acceleration sensitivity of ±2 g, ±4 g, ±8 g, or ±16 g. Exemplary strain-based sensors include a piezo-resistive metal thin film set in a substrate such as a silicone or rubber elastomer substrate.

Controller 320 may be configured to sample data from sensor array 310 at any preferred rate (e.g., 4 kHz or below) that allows for small (e.g., 0.1-5 mm) patient movements to be measured. In some embodiments, sensor data may be collected from the sensor array 310 following the $I^2C$ communication protocol using controller 320, which may receive the accelerator data from each accelerometer at, for example, an exemplary frequency of 30.5 Hz. Controller 320 may then communicate the sampled accelerometer data to a PC for processing according to, for example, one or more processes described herein. Components of system 300 may communicate via wired and/or wireless means and, in some embodiments, may communicate using a communication network like the Internet.

In some embodiments, the sensors of sensor array 310 and/or controller 320 may be physically/electrically coupled to one another and/or other components of system 300. Additionally, or alternatively, one or more of the sensors of sensor array 310 and/or controller 320 may be wirelessly coupled to one another and/or other components of system 300 via, for example, a wireless or near-field communication protocol (e.g., BLUETOOTH™). When the sensors of sensor array 310 and/or controller wire 320 are configured for wireless communication they may include a wireless antenna and/or transceiver (not shown).

System 300 may also include a database 340 configured to store data received by computer system 330, a display device 350 communicatively coupled to computer system 330, and a camera 360, which may be a video camera configured to capture video images of a patient while he or she breathes. In one embodiment, a camera 360 is a high speed camera configured to capture, for example, 1,500-3,000 frames per minute. Two or more components of system 300 may be communicatively coupled to one another via, for example, a network 305 such as the Internet.

Figure 3B:
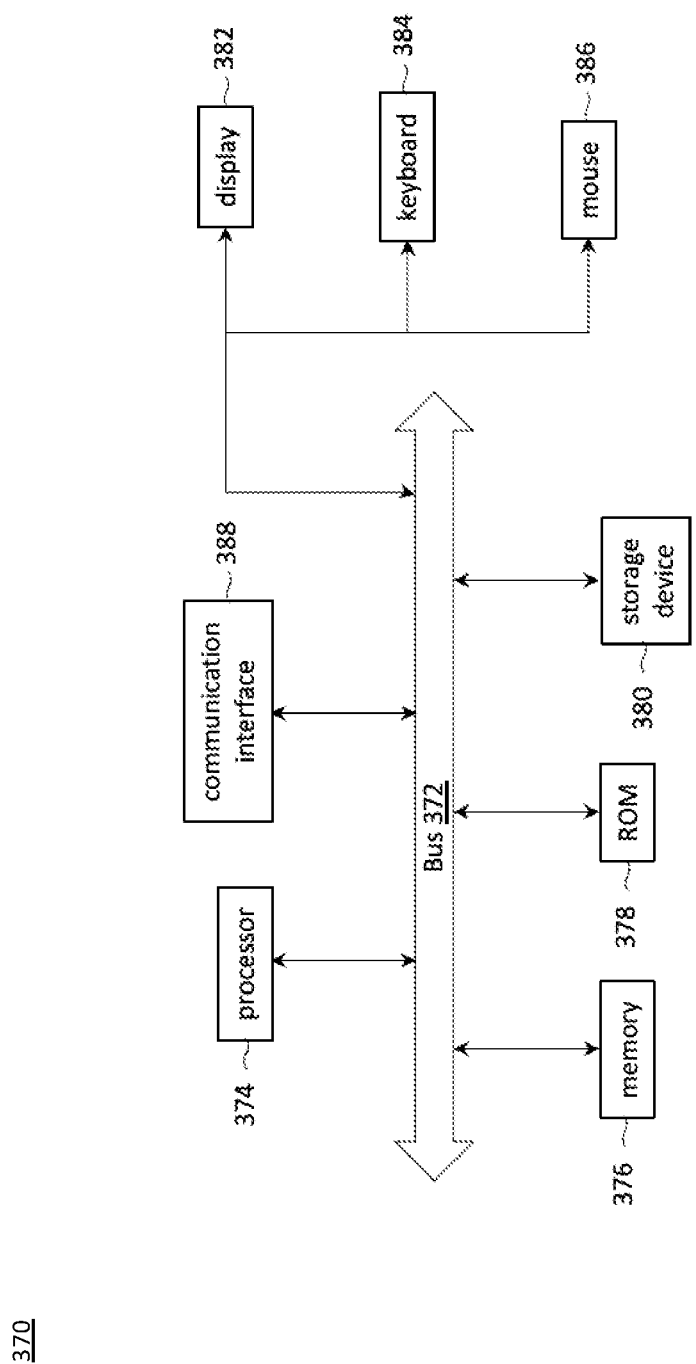
FIG. 3B is a block diagram showing an exemplary computer system, in accordance with embodiments of the present invention.

FIG. 3B is a block diagram showing an exemplary computer system 370 that includes a bus 372 or other communication mechanism for communicating information, and a processor 374 coupled with the bus 372 for processing information. Computer system 370 also includes a main memory 376, such as a random-access memory (RAM) or other dynamic storage device, coupled to the bus 372 for storing information and instructions to be executed by processor 374. Main memory 376 also may be used for storing temporary variables or other intermediate information during execution of instructions to be executed by processor 374. Computer system 370 further includes a read only memory (ROM) 378 or other static storage device coupled to the bus 372 for storing static information and instructions for the processor 374. A storage device 380, for example a hard disk, flash memory-based storage medium, or other storage medium from which processor 374 can read, is provided and coupled to the bus 372 for storing information and instructions (e.g., operating systems, applications programs and the like).

Computer system 370 may be coupled via the bus 372 to a display 382, such as a flat panel display, for displaying information to a computer user. An input device 384, such as a keyboard including alphanumeric and other keys, may be coupled to the bus 372 for communicating information and command selections to the processor 374. Another type of user input device is cursor control device 386, such as a mouse, a track pad, or similar input device for communicating direction information and command selections to processor 374 and for controlling cursor movement on the display 382. Other user interface devices, such as microphones, speakers, etc. are not shown in detail but may be involved with the receipt of user input and/or presentation of output.

The processes referred to herein may be implemented by processor 374 executing appropriate sequences of computer-readable instructions contained in main memory 376. Such instructions may be read into main memory 376 from another computer-readable medium, such as storage device 380, and execution of the sequences of instructions contained in the main memory 376 causes the processor 374 to perform the associated actions. In alternative embodiments, hard-wired circuitry or firmware-controlled processing units may be used in place of or in combination with processor 374 and its associated computer software instructions to implement the invention. The computer-readable instructions may be rendered in any computer language.

In general, all of the above process descriptions are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 370 or similar electronic computing device, that manipulates and transforms data represented as physical (electronic) quantities within its registers and memories into other data similarly represented as physical quantities within its memories or registers or other such information storage, transmission or display devices.

Computer system 370 also includes a communication interface 388 coupled to the bus 372. Communication interface 388 may provide a two-way data communication channel with a computer network, which provides connectivity to and among the various computer systems discussed above. For example, communication interface 388 may be a local area network (LAN) card to provide a data communication connection to a compatible LAN, which itself is communicatively coupled to the Internet through one or more Internet service provider networks. The precise details of such communication paths are not critical to the present invention. What is important is that computer system 370 can send and receive messages and data through the communication interface 388 and in that way communicate with hosts accessible via the Internet. It is noted that the components of system 370 may be located in a single device or located in a plurality of physically and/or geographically distributed devices.

Figure 4A:
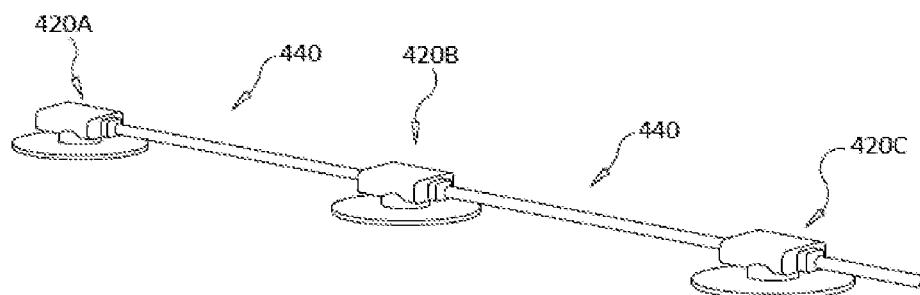
FIG. 4A is an illustration of an exemplary sensor array that includes three sensor modules, in accordance with embodiments of the present invention.
Figure 4B:
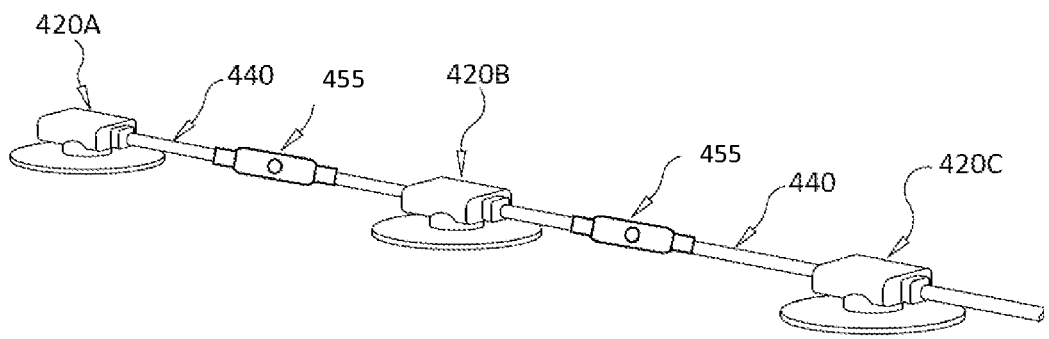
FIG. 4B is an illustration of another exemplary sensor array, in accordance with embodiments of the present invention.
Figure 4C:
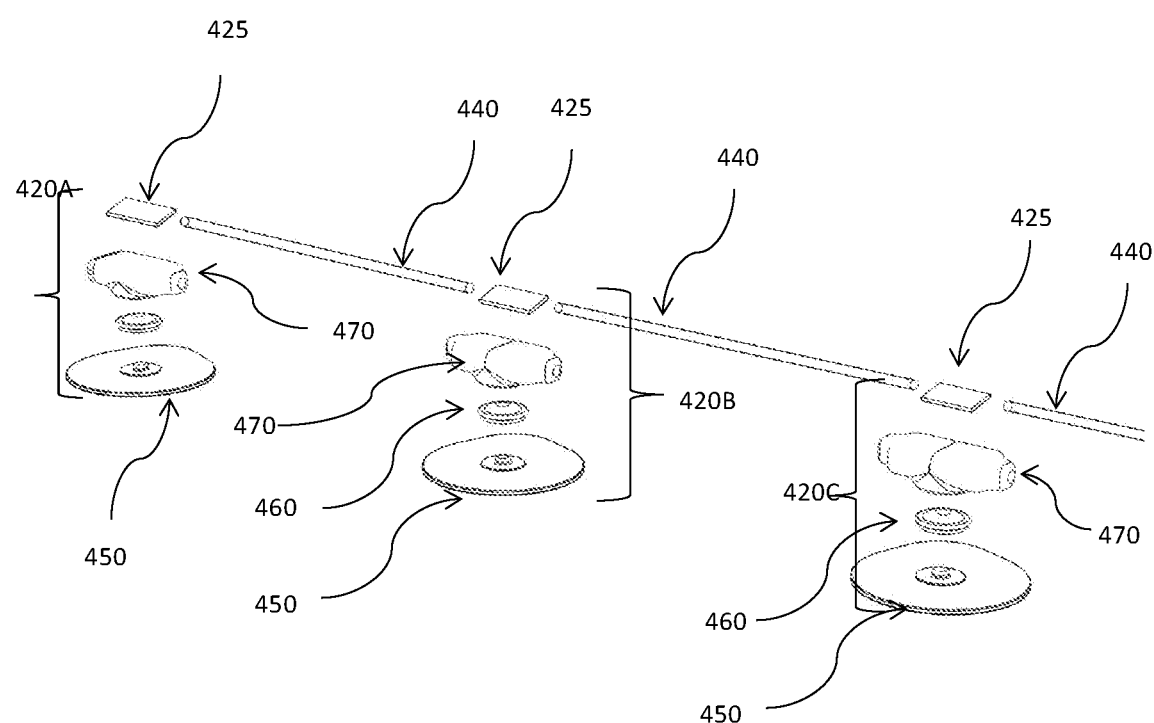
FIG. 4C provides an exploded view of sensor array, in accordance with embodiments of the present invention.

FIG. 4A is an illustration of an exemplary sensor array 310 that includes three sensor modules 420: a first sensor module 420A, which may be configured to be positioned on a patient's chest (and may be sometimes referred to herein as a "chest sensor"), a second sensor module 420B, which may be configured to be positioned on a patient's xiphoid process (and may be sometimes referred to herein as a "xiphoid sensor"), and a third sensor module 420C, which may be configured to be positioned on a patient's abdomen (and may be sometimes referred to herein as a "abdomen sensor") as shown in, for example, FIG. 4C. First, second, and third sensors 420A, 420B, and 420C may be, for example, accelerometers, strain gauges, and/or force meters that are physically and electrically coupled (in series and/or parallel) to one another via by a plurality (e.g., 4, 8, 10) of wires that may be included in a single, or multiple, cable(s) 440. The individual wires/cables 440 may be soldered to leads provided by first, second, and third sensors 420A, 420B, and 420C. Although shown as wired, first, second, and third sensors 420A, 420B, and 420C may, in some cases, be configured to transmit the signals wirelessly or in differing numbers of wiring configurations. Sensor array 310 may be coupled to controller 320 via wire 440. In some cases, wire 440 may be long enough to accommodate placement of the controller a preferred distance (e.g., 10 or 15 feet) away from the patient on whom the sensor array 310 is placed. In some embodiments, wires/cables 440 may be sized to fit different body sizes (e.g., infant, pediatric, adolescent, and adult). Additionally, or alternatively, wires/cables 440 may be of an adjustable length via, for example, spool or retraction mechanism present in a housing for one or more of sensors 420 that facilitate the extension and/or retraction of wires/cables 440 to fit different body sizes. In some embodiments, the wires/cables 440 may be flexible and/or an attachment mechanism between the wires/cables 440 and the sensor is flexible.

FIG. 4B is an illustration of another exemplary sensor array 310 that includes three sensor modules 420 similar to those shown in FIG. 4A. Along with the components of sensor array shown in FIG. 4A, the sensor array 310 of FIG. 4B includes a wire expansion mechanism 455 that may be configured to make a length of a cable/wire 440 adjustable via, for example, retraction and/or expansion by way of a spool or elastic mechanism.

FIG. 4C provides an exploded view of sensor array 310 where each sensor 420 includes a set of sensor circuitry and/or mechanics 425 configured to, for example, sense movement or acceleration, a detachable adhesive patch 450 configured to adhere to the skin of a patient, a clip 460 that may attach to, for example, an electro cardio gram (ECG) pad, and a case 470 that houses clip 460 and sensor circuitry and/or mechanics 425. Sensor circuitry and/or mechanics 425 may be, for example, a printed circuit board that, in some cases includes a MEMS IMU and supporting hardware, a force sensor device, a stress gauge, and/or an accelerometer. Sensor array 310 of FIG. 4D also shows lengths of wire 440.

The spacing of sensors 420 and/or sensor circuitry and/or mechanics 425 may be configured to align with anatomical measurements of the distance between the chest and xiphoid process and between the xiphoid and apex of the abdomen of a patient and may be of differing lengths to accommodate differing ages and body types, such as a children 1 to 5 years of age, an adolescent 13-15 years of age, or an adult (18-90 years of age). In some cases, a length of one or more wires 440 may be adjustable in order to accommodate, for example, different body types/sizes. For example, a housing for one or more sensors 420 may include a mechanism (e.g., spool) that may enable one or more wires 440 to retract into the housing. Additionally, or alternatively, a component of a sensor array may be elastic or otherwise configured to expand or contract so that positioning between sensors 420 may accommodate the physiology of an individual. In some embodiments, a first accelerometer 420 may be configured to be placed on the wearer's chest (e.g., a midpoint between the patient's nipples), a second accelerometer 420 may be configured to be placed on the patient's xiphoid process, and a third accelerometer 420 may be configured to be placed on the patient's abdomen.

Figure 4D:
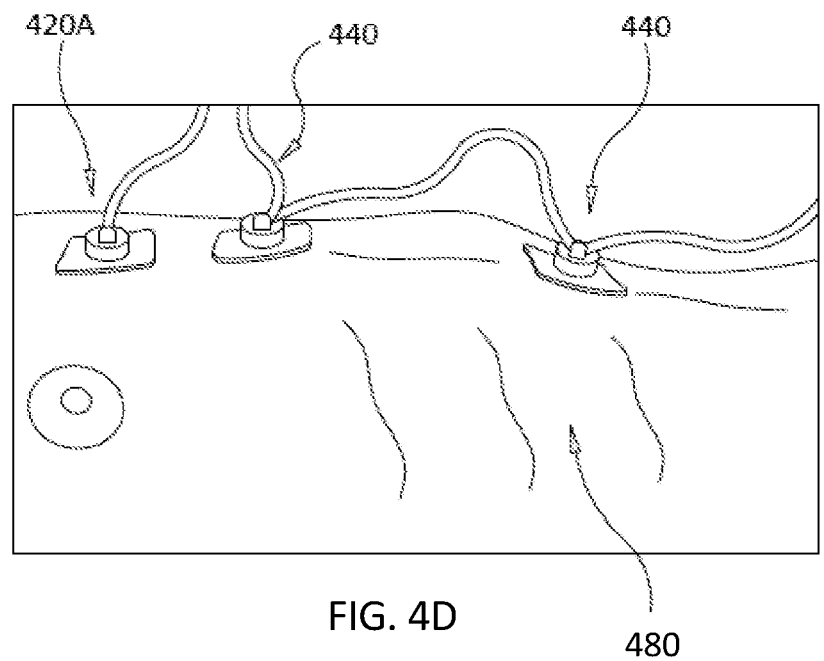
FIG. 4D is an illustration of a patient with a sensor array positioned thereon, in accordance with embodiments of the present invention.

FIG. 4D is an illustration of a patient 480 with a sensor array 310 positioned thereon. In some cases, sensor array 310 may be positioned onto patient 480 when the user (e.g., heath care provider) adheres the first sensor 420A at the midpoint between the nipples, adheres the second sensor 420B on the epidermis proximate to the patient's xiphoid process, and adheres the third sensor 420C onto the abdomen approximately 1-3 inches above the navel for a pediatric patient, or 2-6 inches above the navel for an adult patient.

Figure 5A:
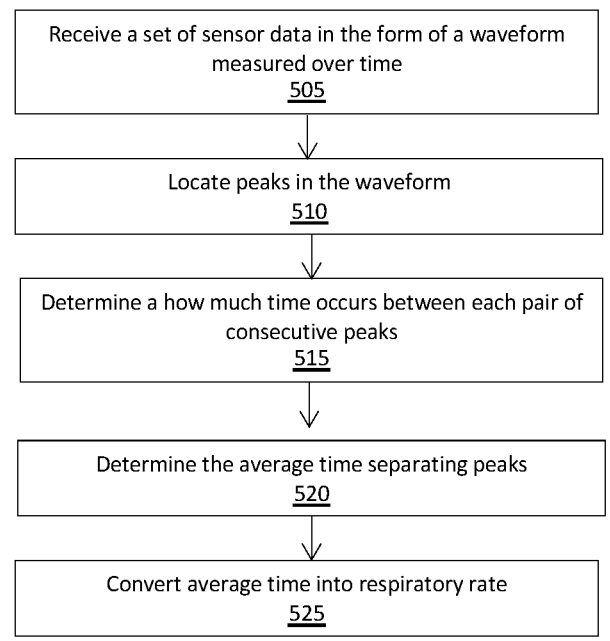
FIG. 5A is a flowchart showing exemplary steps of a process for determining a patient's respiratory rate, in accordance with embodiments of the present invention.

FIG. 5A is a flowchart showing exemplary steps of a process 500 for determining a patient's respiratory rate. Process 500 may be executed by, for example, system 300 or any component thereof.

Figure 5B:
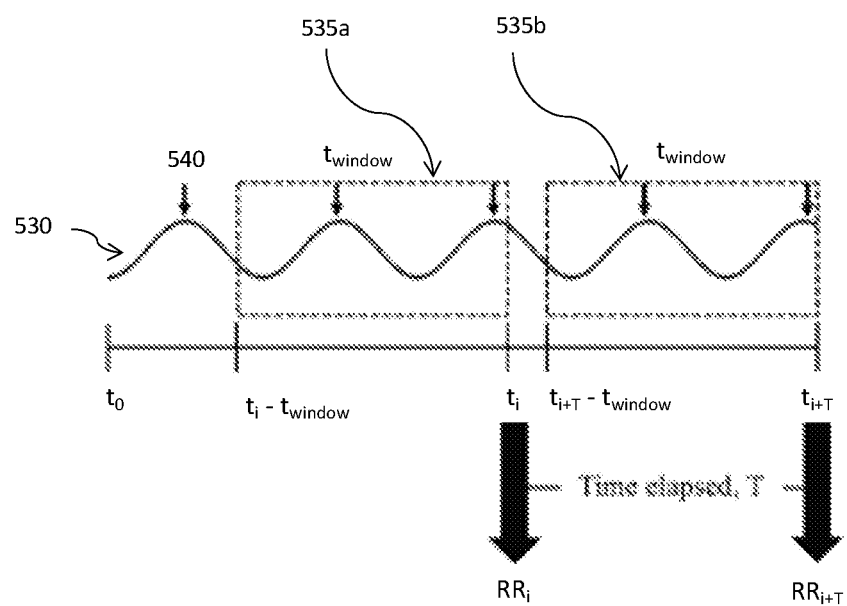
FIG. 5B depicts a graph of a waveform that may represent received sensor data, in accordance with embodiments of the present invention.

Initially, in step 505, sensor data may be received in the form of, for example, a waveform 530 with a plurality of peaks 540 as shown in FIG. 5B. Oftentimes, the sensor data received is data from an abdominal sensor like abdominal sensor 420C. The sensor data may be time stamped and/or divided into a plurality of time windows examples of which are shown in FIG. 5B as first time window 535a and second time window 535b. In some embodiments, the sensor data may be filtered using, for example, a bandwidth filter.

The received sensor data may then be analyzed using, for example, a peak detection function to detect peaks in the sensor data (step 510). These peaks may correspond to a maximal expansion of the abdominal cavity, which occurs once per respiratory cycle and thus are correlated with the respiratory cycle of the patient. In some cases, peaks in the data may be characterized by a threshold separation by a number of points and a threshold prominence relative to surrounding local maxima, whereby threshold separation means that each peak is separated by a certain number of points. For example, if a peak is identified at point x and threshold separation is defined as 10 points, that means the earliest another peak can be identified is at point x+10. This prevents peaks from being sampled from the data too frequently. Separation may be equivalent to a distance input for the python function disclosed herein. Threshold prominence may provide an indicator of relative amplitude. Noise within a signal has some typical amplitude, and the signal content of interest (e.g., amplitude or number of breaths in a sample) may have a common, or typical, amplitude. Setting a prominence threshold allows you to set how "prominent" a peak has to be relative to other possible peaks to be actually marked as a peak.

In step 515, a duration of time separating each pair of consecutive peaks may be determined for a plurality of peaks and/or time windows. Then, an average value for the time separating the peaks may be determined (step 520) and this average time value may be converted into a respiratory rate (step 525) wherein, for example, an average number of peaks within a given time window (e.g., 1 minute) corresponds to a number of breaths per minute (i.e., respiratory rate).

Figure 6:
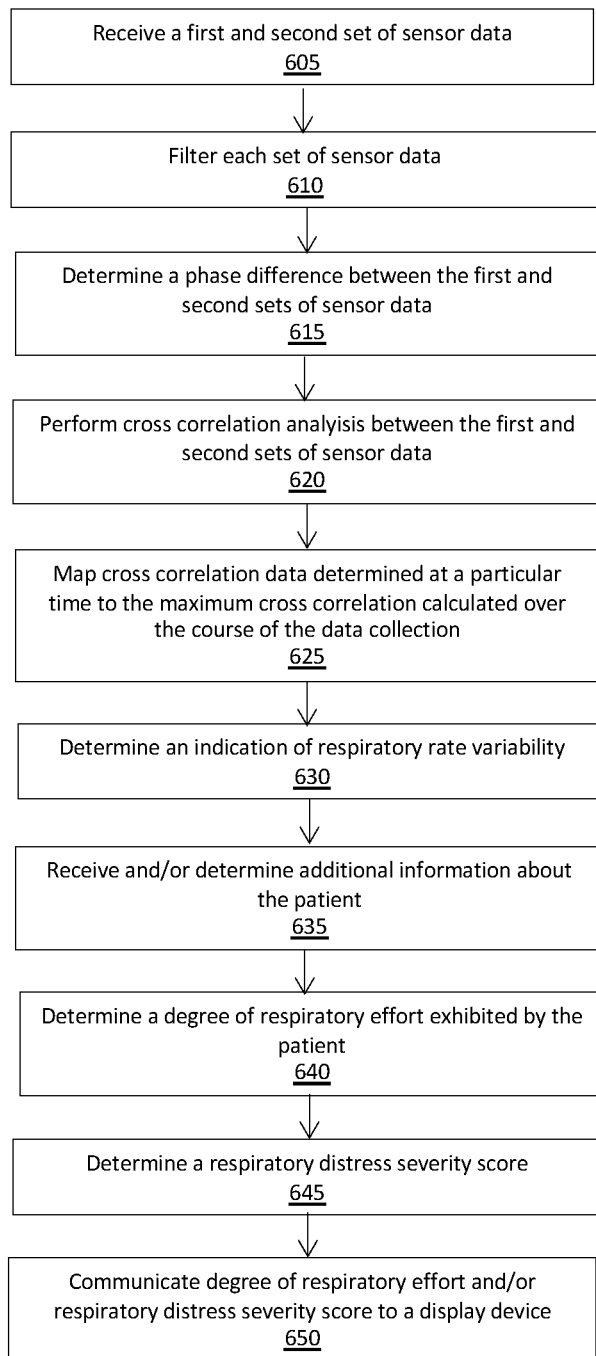
FIG. 6 is a flowchart showing exemplary steps of a process for determining a patient's TAA, a degree of respiratory distress exhibited by the patient, and/or a respiratory distress score for the patient, in accordance with embodiments of the present invention.

FIG. 6 is a flowchart showing exemplary steps of a process 600 for determining a patient's TAA, a degree of respiratory distress exhibited by the patient, and/or a respiratory distress score for the patient. These determinations may be performed on, for example, a periodic, as-needed, and/or continuous basis. Process 600 may be executed by, for example, system 300 or any component thereof such as sensor array 310.

Initially, a first and second set of sensor data may be received by a processor or computer like computer system 330 (step 605). In some embodiments, the first and second sets of sensor data are waveforms like those shown in FIGS. 2A-2C. The sensor data may be received from, for example, a controller like controller 320 and/or a sensor like first sensor 420A, second sensor 420B, and/or third sensor 420C. The sensor data may correspond to, for example, acceleration data, a force measurement, a strain measurement, and/or a measured change in diameter of, for example the thorax, chest, xiphoid process area, and/or abdomen of a patient and may be taken over time (e.g., 30 s, 1 minute, 5 minutes, etc.). At times, data corresponding to multiple measurements may be received in step 605. For example, data corresponding to a measurement taken at the patient's chest from, for example, first sensor 420A, data corresponding to a measurement taken at the patient's xiphoid process from, for example, second sensor 420B, and/or data corresponding to a measurement taken at the patient's abdomen from, for example, third sensor 420C may be received in step 605. In some embodiments, different types of data corresponding to a measurement taken from a particular location (e.g., chest, xiphoid process, and/or abdomen) may be received in step 605. For example, data corresponding to acceleration, force, and/or strain measurements for one or more of the particular locations on the patient's chest may be received so that, for example, multiple types of measurements may be used to validate and/or establish a confidence level for an accuracy of determinations using the received data.

The received sensor data may then be filtered, analyzed, and/or pre-processed (step 610). In some cases, the analysis and pre-processing of step 610 may include, for example, filtering the data and/or performing a phase shift analysis using, for example, a Hilbert transform filter so that a phase angle between the resulting functions may be determined (step 615).

The Hilbert transform filter is a mathematical function that can be used to convert real signals into analytic signals, defined as signals with no-negative frequency components. A continuous time analytic signal can be represented as Equation 1, below:

$$z(t) = \frac{1}{2\pi}\int_0^\infty Z(\omega)e^{j\omega t}d\omega \qquad \text{Equation 1}$$

Where:
z(t)=Analytic representation
t=time
Z($\omega$)=the complex coefficient of the positive-frequency signal and sets its amplitude and phase;
$\omega$=frequency
d$\omega$=the derivative of the frequency Real sinusoids can be converted to positive frequency complex sinusoids by generating a phase quadrature component to serve as the imaginary part; this phase-quadrature component is generated by shifting the original signal by 90°. The Hilbert transform filter has the effect of filtering out negative frequencies and creating a gain of 2 for positive frequencies.

The Hilbert transform can be explained mathematically wherein if two signals are perfectly synchronous, the resulting phase angle approaches 0° while during paradoxical motion phase angle approaches 180°.

The Hilbert transform can be explained mathematically by the following calculations of Equations 2A and 2B where x(t) is a sinusoidal signal with unit amplitude, frequency $\omega_0$, positive frequency components $X_+$ and negative frequency components $X_-$ where:

$$x_+(t) \triangleq e^{j\omega_0 t} \qquad \text{Equation 2A}$$

$$x_-(t) \triangleq e^{-j\omega_0 t} \qquad \text{Equation 2B}$$

Application of a −90° phase shift $$\left(e^{-\frac{j\pi}{2}}\right)$$

to the positive frequency component ($X_+$) and a +90° phase shift $$\left(e^{\frac{j\pi}{2}}\right)$$

to the negative frequency component ($X_-$) is represented by Equations 3A and 3B, respectively.

$$y_+(t) = -je^{j\omega_0 t} \qquad \text{Equation 3A}$$

$$y_-(t) = je^{-j\omega_0 t} \qquad \text{Equation 3A}$$

Then, adding the original and shifter components together as a single signal (x(t)+jy(t)) yields Equations 4A and 4B, reproduced below.

$$z_+(t) = e^{j\omega_0 t} - j^2 e^{j\omega_0 t} = 2e^{j\omega_0 t} = 2x_+(t) \qquad \text{Equation 4A}$$

$$z_-(t) = je^{-j\omega_0 t} + j^2 e^{-j\omega_0 t} = 0 \qquad \text{Equation 4B}$$

In processing of discrete time signals using software such as MATLAB and/or the Python script library, the Hilbert transform is computed by first calculating the Fourier transform of the signal. The amplitude of the negative frequency components of the signal is then set to zero. Finally, a new signal is generated by calculating the inverse Fourier transform of the new frequency space.

Figure 8:
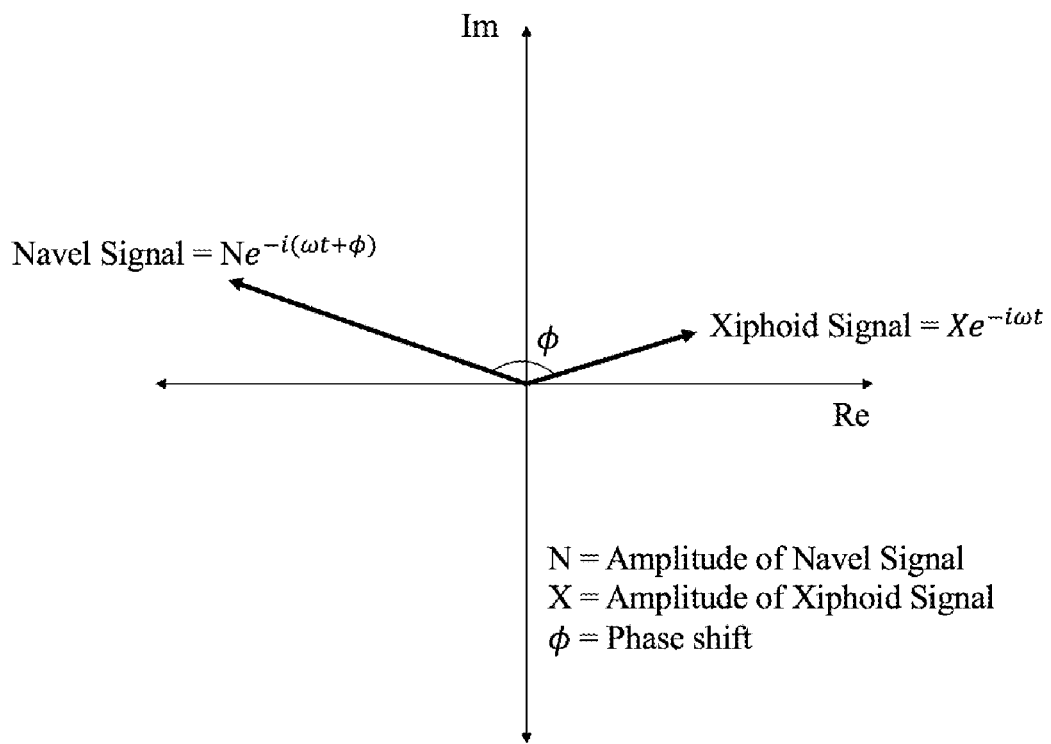
FIG. 8 provides a graph wherein a phase shift Ø between the Hilbert transform-filtered amplitude of data received from a sensor placed proximate to the patient's navel or abdomen, in accordance with embodiments of the present invention.

Using the Hilbert transform may allow for signals that are approximately sinusoidal, such as respiratory signals, to be defined with a single characteristic frequency. In some embodiments, determining the characteristic frequency of the data from two or more positions/sensors on the patient's body (e.g., xiphoid and navel positions) may allow for the determination of a phase shift between the signals. This may be done after identifying the window of recently collected data over which phase shift may be calculated and normalizing the data by subtracting away the mean of the data points contained within the window and dividing by the standard deviation. Once normalized, the data may be sent through a Hilbert transform filter and phase shift may be calculated. FIG. 8 provides a graph 800 wherein a phase shift Ø between the Hilbert transform-filtered amplitude of data received from a sensor placed proximate to the patient's navel or abdomen (sometimes referred to herein as the third signal) and referred to in FIG. 8 as a navel, signal (N) and data received from a sensor placed proximate to the patient's xiphoid process (sometimes referred to herein as the second signal) and referred to in FIG. 8 as a xiphoid, signal (X) are plotted in the complex plane where the Y-axis corresponds to imaginary numbers (labeled Im on graph 800) and the X-axis corresponds to real numbers (labeled Re on graph 800). The navel signal (N) may be expressed as Equation 5, below:

$$\text{Navel Signal} = Ne^{-i(wt+\emptyset)} \qquad \text{Equation 5}$$

Where:
N=amplitude shift of the navel signal
e=Euler's number (approximately 2.71828)
ω=frequency
Ø=phase shift
t=time The xiphoid signal may be expressed as Equation 6, below:

$$\text{Xiphoid Signal} = Xe^{-iwt} \quad \text{Equation 6}$$

Where:
X=amplitude shift of the xiphoid signal
e=Euler's number (approximately 2.71828)
ω=frequency
t=time Optionally, in step 620, a cross-correlation analysis of the two sets of data received in step 605 (e.g., data from the second and third sensors) may be performed in addition and/or alternatively to the phase difference determination of step 615. Results of the cross-correlation analysis (also referred to herein as cross-correlation data) for a moment in particular time may be mapped to the maximum cross correlation calculated over the course of data collection (step 625). The course of data collection may occur for a time period lasting, for example, 15 seconds, 30 seconds, 60 seconds, 5 minutes, 10 minutes and/or an hour. In some cases, the collection of data may be continuous and/or periodic over a longer period of time (e.g., 4, 12, 24, 48, or 82 hours). In some embodiments, the cross-correlation analysis may be based upon time integration of the two or more signals. For example, the cross-correlation determined at a given time may be mapped from 0 to 100% relative to the maximum cross correlation calculated over the course of the data collection; this output, or mapping, may be referred to as the "relative cross correlation". The phase shift analysis of step 615 and/or the cross correlation analysis of step 620 may be performed over time periods in a manner similar to how the respiratory rate calculation is performed via process 500.

In some embodiments, the cross-correlation of two discrete functions f[n] and g[n], or data sets, may be defined as shown in Equation 8, below:

$$(f \star g)[n] \equiv \sum_{m=-\infty}^{\infty} f^*[m]g[m+n] \quad \text{Equation 8}$$

Figure 9:
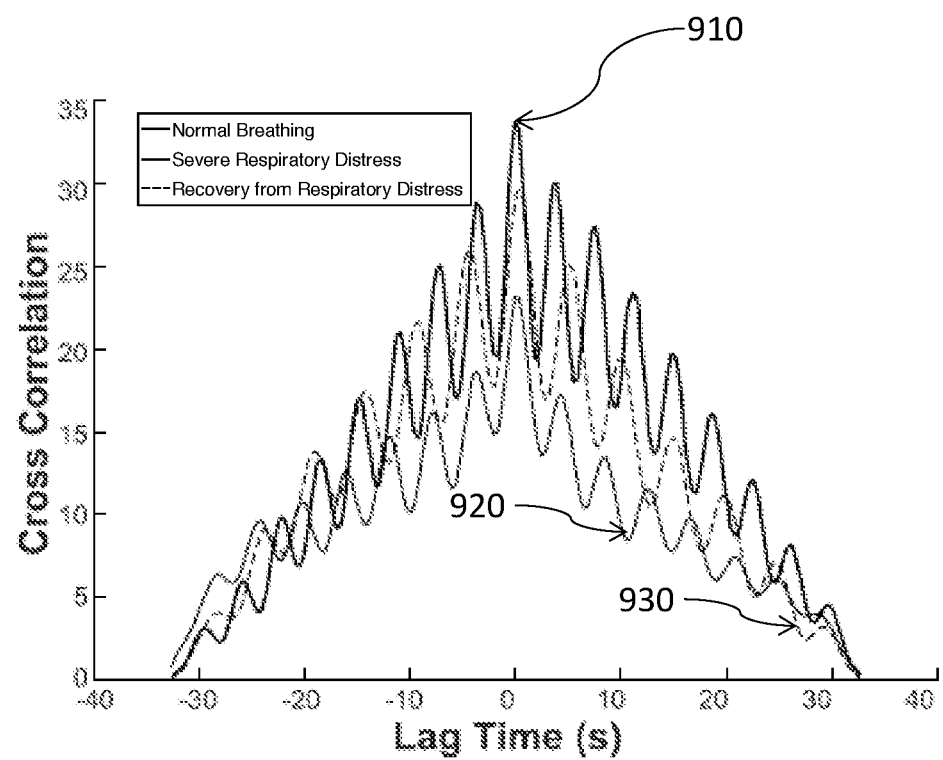
FIG. 9 provides a graph that shows a motion capture test, in accordance with embodiments of the present invention.

Where:
f=a signal corresponding to a first data set
g=a signal corresponding to a second data set
n=a lag between functions
m=maximum value of a signal corresponding to either the first or second data set over a period of time For two noise distorted, approximately periodic discrete signals with equal periods, the cross-correlation function of two signals with lag n ranging from the negative to the positive sum of the number of points in each signal may look approximately as shown in FIG. 9, where the maximum will occur at zero lag time and local maxima occur at shifts equal to the period. FIG. 9 provides a graph 900 that shows a motion capture test where lag time in seconds is shown as a function of cross correlation for xiphoid and navel respiratory signals determined during various stages of respiration distress wherein curve 910 shows cross-correlation as a function of lag time for normal breathing, curve 920 shows cross-correlation as a function of lag time for breathing when in severe respiratory distress, and curve 930 shows cross-correlation as a function of lag time for breathing when in recovery from severe respiratory distress. FIG. 9 shows that maximal correlation occurs between the two signals under normal conditions; correlation decreases in severe respiratory distress; and correlation returns to near baseline upon recovery from respiratory distress.

Optionally, in step 630, an indication of a respiratory rate variability of the patient may be received. This indication may be determined using the first and second sets of sensor data and/or may be input from another device and/or attending care giver.

Optionally, in step 635, additional information about the patient may be received and/or determined. Exemplary received additional information includes information pertaining to a physiological characteristic of the patient such as body mass index (BMI), a thickness of adipose tissue on the patient's abdomen, a weight of the patient, a size of the patient, the patient' respiratory rate (e.g., breaths per minute), mental status, blood oxygen saturation, and/or whether the patient is on supplemental oxygen or other respiratory assistance. Exemplary determined additional information includes respiratory rate (e.g., breaths per minute) which may be determined using, for example, a process like process 500 described above with regard to FIG. 5A, as well as respiratory rate s, a measure of the variation in length of time of each respiratory cycle.

In step 640, the phase shift analysis data, mapped cross-correlation data and/or the additional information received in step 635 may be used to determine a degree of respiratory effort exhibited by the patient, which may be used to determine a level of respiratory distress (i.e., a respiratory distress score) for the patient (step 645), where decreased cross-correlation and increased phase shift between two or more collected signals indicate increased thoraco-abdominal asynchrony (TAA). In some cases, the degree of respiratory effort exhibited by the patient may be, and/or may include a degree of TAA exhibited by the patient. The degree of respiratory effort and/or respiratory distress may then be provided to a display device such as a computer monitor or other display device (step 650).

In some embodiments, not all of the steps of process 600 are performed to determine a degree of respiratory distress (step 640) and/or determine a respiratory distress severity score (step 645). For example, in some embodiments, the determinations of steps 640 and/or 645 are performed using only the phase difference of step 615, a result of the cross-correlation analysis of step 620, a mapping of the cross-correlation data of step 625, a determination of an indication of respiratory variability of step 625. Alternatively, a result of execution of two or more steps of process 600 may be used to determine a degree of respiratory distress (step 640) and/or determine a respiratory distress severity score (step 645). For example, a combination of results from execution of steps 615 and 620, combination of results from execution of steps 615, 620, and 625, combination of results from execution of steps 615, 620, 625, and 630, combination of results from execution of steps 620, 625, and/or 630, and/or a combination of results from execution of steps 625 and 630 may be combined to determine a degree of respiratory distress (step 640) and/or determine a respiratory distress severity score (step 645).

Figure 7:
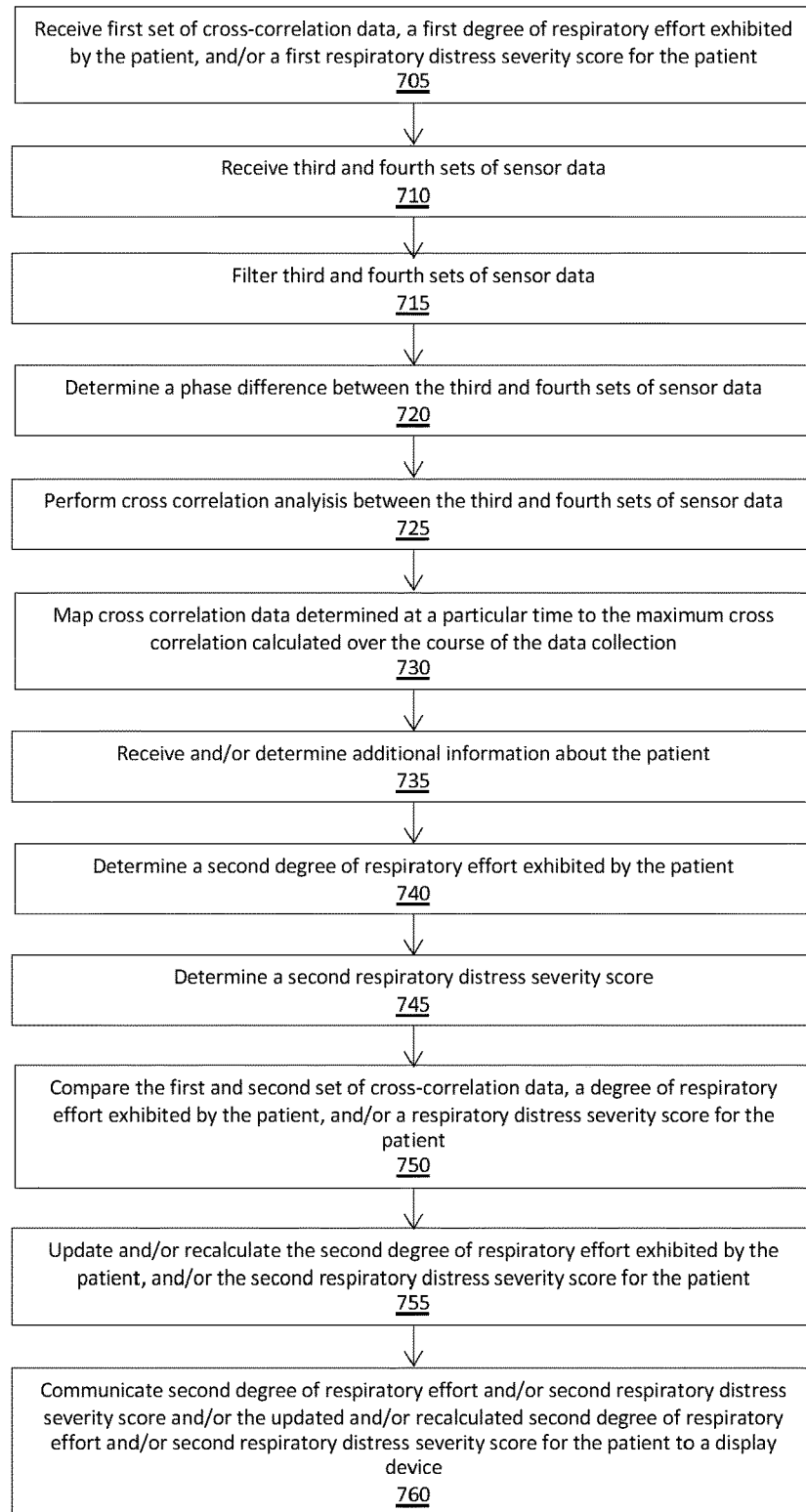
FIG. 7 is a flowchart showing exemplary steps of another process for determining a patient's TAA, a degree of respiratory distress exhibited by the patient, and/or a respiratory distress score for the patient, in accordance with embodiments of the present invention.

FIG. 7 is a flowchart showing exemplary steps of another process 700 for determining a patient's TAA, a degree of respiratory distress exhibited by the patient, and/or a respiratory distress score for the patient. These determinations may be performed on, for example, a periodic, as-needed, and/or continuous basis. Process 700 may be executed by, for example, system 300 or any component thereof such as sensor array 310.

Initially, in step 705, a first set of cross-correlation data, a first degree of respiratory effort exhibited by the patient, and/or a first respiratory distress severity score for the patient may be received via, for example, execution of process 600 or a portion thereof. In some embodiments, the information received in step 705 may be a baseline set of cross-correlation data, a baseline respiratory effort exhibited by the patient, and/or a baseline respiratory distress severity score that, in some cases may be previously determined as part of, for example, a routine medical exam. These baselines may assist with the establishment of how much effort a patient exhibits while breathing under normal conditions for the patient (e.g., not when acutely ill). Using baselines in this way may allow determinations of respiratory effort to factor in individual differences when determining whether or not the patient is in respiratory distress and/or quantifying a degree of respiratory distress or determining a respiratory distress score for the patient. This may be helpful when, for example, the patient exhibits impaired breathing under normal conditions as may be the case with a chronic respiratory diagnosis (e.g., asthma, chronic pulmonary obstructive disease (COPD), or lung cancer). Additionally, or alternatively, the information received in step 705 may be a set of cross-correlation data, a degree of respiratory effort exhibited by the patient, and/or a respiratory distress severity score determined for the patient prior (e.g., minutes, hours, days) to execution of process 700.

In step 710, a third and a fourth set of sensor data may be received by a processor or computer like computer system 330. In some embodiments, the third and fourth sets of data are from different sensors positioned on different portions of the patient's body (e.g., chest and abdomen or xiphoid process and abdomen). In some embodiments, the third and fourth sets of sensor data are waveforms like those shown in FIGS. 2A-2C and, at times, the third and fourth sets of sensor data may be similar to the first and second sets of sensor data received in step 605.

The received sensor data may then be filtered, analyzed, and/or pre-processed (step 715). Execution of step 715 may be similar to execution of step 610 described above with the exception that the filtering, analysis, and/or pre-processing is performed on the third and fourth sets of sensor data. Then, a phase difference between the third and fourth sensor data sets may be determined (step 720). Execution of step 720 may be similar to execution of step 615.

A cross-correlation analysis of the third and fourth sets of data may then be performed (step 725) and the results of this cross-correlation analysis (also referred to herein as cross-correlation data) for a moment in particular time may be mapped to the maximum cross correlation calculated over the course of data collection (step 730). In some embodiments, execution of steps 725 and 730 may be performed in a manner similar to execution of steps 620 and 625, respectively.

Optionally, in step 735, additional information about the patient may be received and/or determined. The additional information received in step 735 may be similar to the additional information received in step 635.

In step 740, the mapped cross-correlation data for the third and fourth data sets and/or the additional information received in step 735 may be used to determine a second, or subsequent, degree of respiratory effort exhibited by the patient, which may be used to determine a second, or subsequent, level of respiratory distress (i.e., a respiratory distress score) for the patient (step 745). In some cases, the degree of respiratory effort exhibited by the patient may be, and/or may include a degree of thoraco-abdominal asynchrony (TAA) exhibited by the patient.

In step 750, the mapped cross-correlation data for the third and fourth data sets may be compared with the mapped cross-correlation data for the third and fourth data sets in order to determine a difference therebetween. This difference may be used to adjust or qualify (e.g., elevated or improving) the second determined degree of respiratory distress determined in step 740 and/or the second respiratory score determined in step 745. Additionally, or alternatively, step 750 may be performed prior to step(s) 740 and/or 745 and the comparison may be used to determine the second degree of respiratory distress determined in step 740 and/or the second respiratory score determined in step 745.

Additionally, or alternatively, step 750 may include a comparison of the degree of respiratory effort received in step 705 with the second degree of respiratory effort determined in step 740. This difference may be used to adjust or qualify (e.g., elevated or improving) the second degree of respiratory distress determined in step 740 and/or the second respiratory score determined in step 745. Additionally, or alternatively, step 750 may be performed prior to step(s) 740 and the comparison may be used to determine the second degree of respiratory distress determined in step 740 and/or the second respiratory score determined in step 745.

Additionally, or alternatively, step 750 may include a comparison of the degree of a respiratory distress score received in step 705 with the second respiratory distress score determined in step 745. This difference may be used to adjust or qualify (e.g., elevated or improving) the second degree of respiratory distress determined in step 740 and/or the second respiratory score determined in step 745. Additionally, or alternatively, step 750 may be performed prior to step(s) 745 and the comparison may be used to determine the second degree of respiratory distress determined in step 740 and/or the second respiratory distress score determined in step 745.

Optionally, in step 755, the second degree of respiratory distress determined in step 740 and/or the second respiratory distress score determined in step 745 may be updated and/or recalculated using the comparison results of step 750.

In step 760, the second degree of respiratory effort and/or second respiratory distress severity score and/or the updated and/or recalculated second degree of respiratory effort and/or second respiratory distress severity score for the patient may be communicated to a display device.

Figure 10:
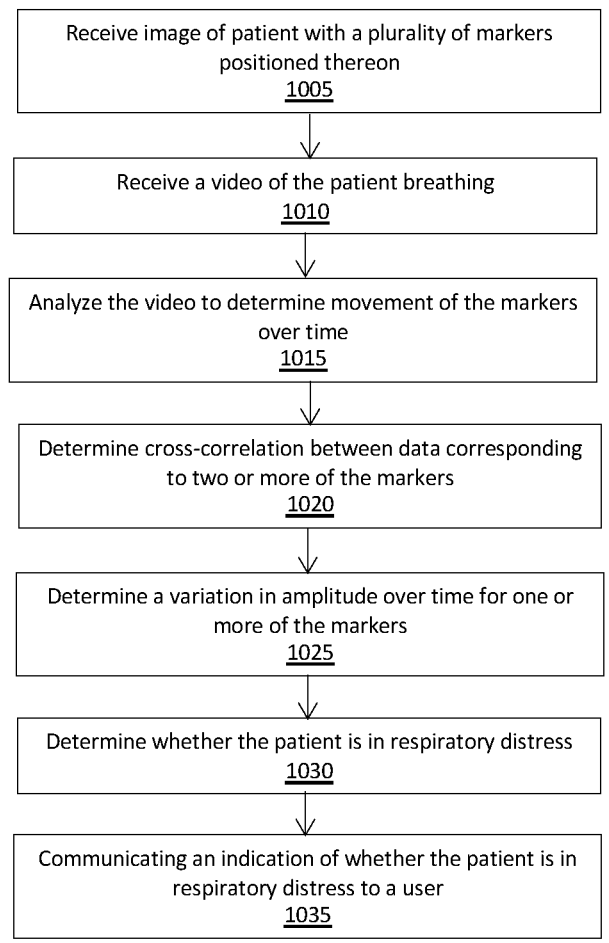
FIG. 10 is a flowchart showing exemplary steps of a process for gathering information regarding movements of a patient's thorax and portions thereof while breathing over time, in accordance with embodiments of the present invention.

FIG. 10 is a flowchart showing exemplary steps of a process 1000 for gathering information regarding movements of a patient's thorax and portions thereof while breathing over time and assessing whether the patient is in respiratory distress using, for example, system 300 and/or components thereof.

In step 1005, an image of a patient with a plurality of markers positioned thereon may be received. The markers may mark, or delineate, different positions on the thorax of the patient. The position of the markers in the image received in step 1005 may represent an original position, or origin, for the marker against which motion up and down, left and right may be measured.

Figure 11:
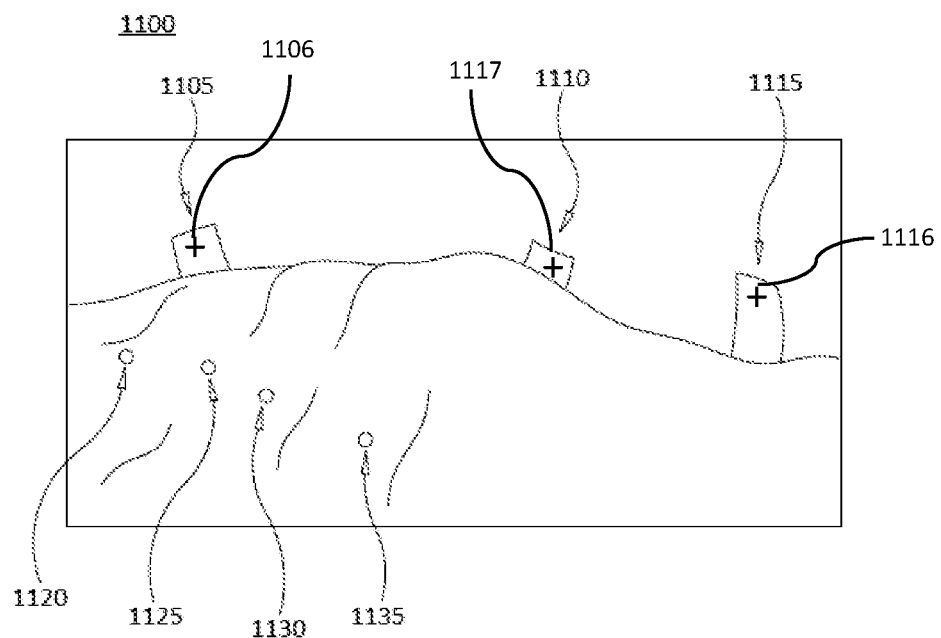
FIG. 11 provides an example of an image that may be received in step where different markers, in the form of dots drawn on the patient and tabs sticking up from the patient delineate different positioned on the patient's thorax, or chest, in accordance with embodiments of the present invention.

FIG. 11 provides an example of an image 1100 that may be received in step 1005 where different markers, in the form of dots drawn on the patient and tabs sticking up from the patient delineate different positions on the patient's thorax, or chest. More specifically, FIG. 11 shows a first marker 1105 positioned on an upper region of the patient's chest, a second marker 1110 positioned below the sternum, a third marker 1115 positioned at, or proximate to, the navel, a fourth marker 1120 positioned in approximately at a first intercostal space (e.g., between the fifth and sixth rib), a fifth marker 1125 positioned in approximately at a second intercostal space (e.g., between the sixth and seventh rib), a sixth marker 1130 positioned in approximately at a third intercostal space (e.g., between the seventh and eighth rib), a seventh marker 1135 positioned in approximately at a fourth intercostal space (e.g., between the eighth and ninth rib). In some embodiments, first, second, and/or third marker 1105, 1110, and/or 1115 may include a first, second, and/or third reference mark 1106, 1117, and/or 1116, respectively, which may be configured to assist with the video capture of movement by the patient while breathing in, for example, the X, Y, and/or Z-direction(s). In some cases, the reference point may be in the form of a crosshair or "+" sign to, for example, aid with analysis of a video recording of the patient to determine movement of the patient while he or she breathes. Also shown in FIG. 11 are optional sub-markers. Motion of the patient's chest and abdomen may be observed and quantified via the first-seventh markers 1105-1135. For example, a video camera, such as video camera 360, may record movements of the patient's chest while breathing and this video may be received in step 1010. The video may be analyzed to, for example, determine movement of the markers over time (step 1015). In some embodiments, a plurality of videos may be received in step 1010 and may be analyzed/quantified via the first-eighth markers under different breathing conditions (e.g., unrestricted and restricted) for the patient. For example, a video recording of patient breathing may be taken when breathing is unrestricted (e.g., normal); when there is resistance applied to the patient's chest and/or breathing via, for example, an elastic band and/or an exercise mask with fixed resistance with no time to acclimate to breathing with resistance; and/or when there is resistance applied to the patient's chest and/or breathing via, for example, an elastic band and/or an exercise mask with fixed resistance with an interval of time (e.g., 3-8 minutes) for the patient to acclimate to breathing with resistance. These recordings may then be analyzed to determine how much first-seventh markers 1105-1135 move over time under the differing conditions for the patient.

Figure 12:
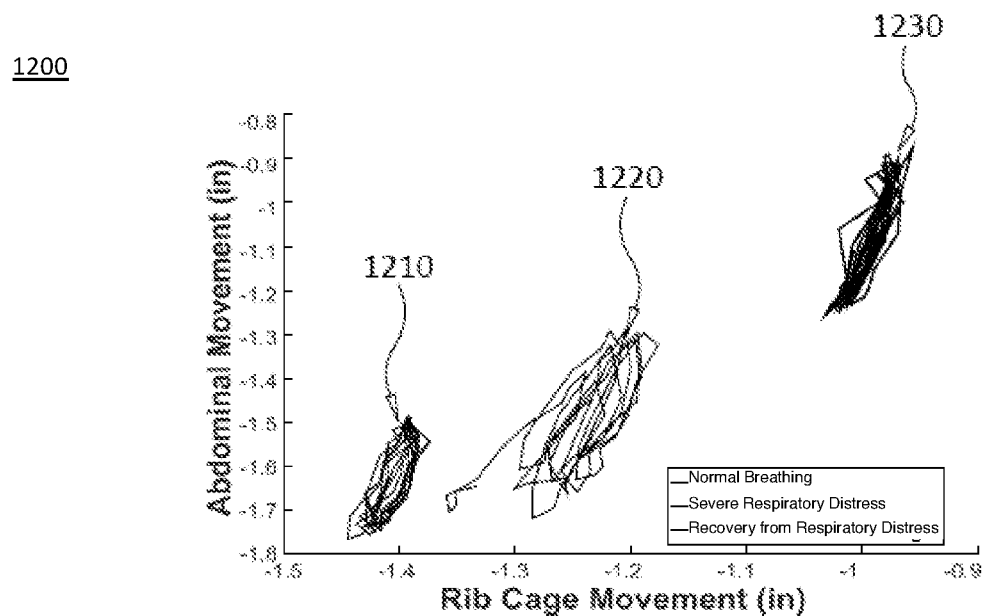
FIG. 12 provides an exemplary graph showing three Lissajous curves that plot abdominal movement as a function of rib cage movement, in accordance with embodiments of the present invention.

FIG. 12 provides an exemplary graph 1200 showing three Lissajous curves that plot abdominal movement in inches as a function of rib cage movement measured in inches where a first Lissajous curve 1210 represents abdominal movement as a function of rib cage movement at when the patient is in recovery from respiratory distress, a second Lissajous curve 1220 represents abdominal movement as a function of rib cage movement when the patient is breathing with severe respiratory distress, and a third Lissajous curve 1230 represents abdominal movement as a function of rib cage movement when the patient experiences normal breathing. The first, second, and third Lissajous curves 1210, 1220, and 1230 reflect variation in amplitude of movement for each of the three types of breathing (i.e., recovery from respiratory distress, severe respiratory distress, and normal breathing, respectively) wherein, for this example, there is a wider range in amplitude for breathing when recovery from respiratory distress as compared to normal breathing (i.e., second and third Lissajous curves 1220 and 1230) and a recovery (i.e., relatively smaller changes in amplitude for abdominal movement compared with rib cage movement) shown by first Lissajous curve 1210 demonstrated by the recovery from respiratory distress breathing. This shows how a comparison for amplitudes of a patient's abdominal and rig cage movement may assist in quantifiably characterizing the extent to which a patient is experiencing respiratory distress.

Optionally, in step 1020, a cross-correlation of the data from two or more of the markers may then be performed in, for example, a manner similar to the cross-correlation analysis of step 620.

Figure 13:
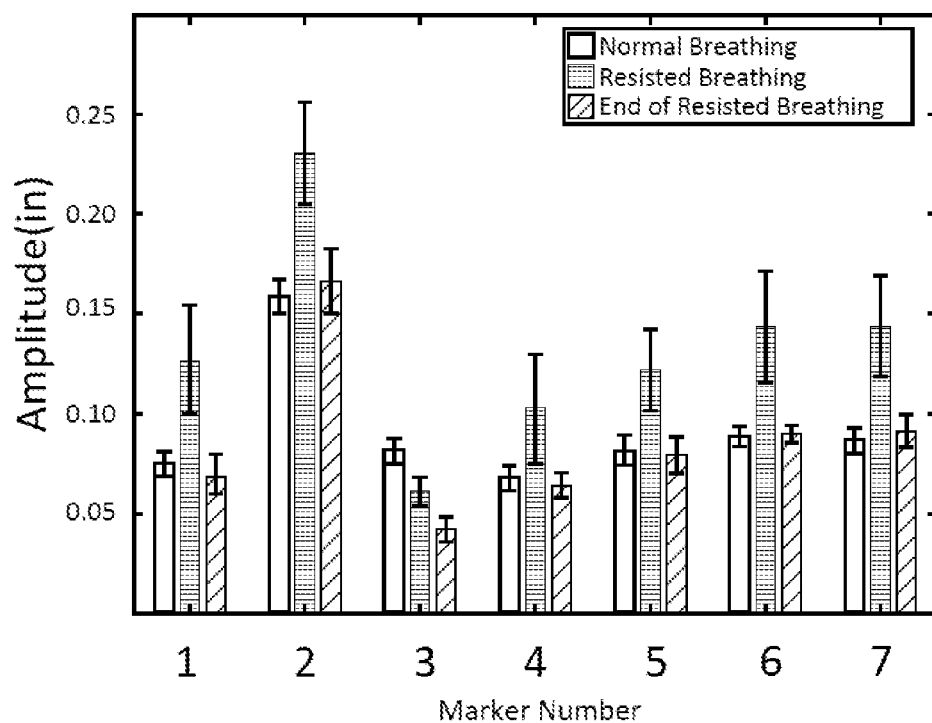
FIG. 13 provides a bar graph of average peak to peak amplitudes during normal breathing with severe respiratory distress, and breathing following recovery from severe respiratory distress, in accordance with embodiments of the present invention.

Optionally, in step 1025, a variation in amplitude for one or more of the markers over time may be determined. As an example, FIG. 13 provides a bar graph of average peak to peak amplitudes during normal breathing (bar graph with no fill (or white)), breathing with severe respiratory distress (shown with bar graphs with dashed horizontal fill lines), and breathing following recovery from severe respiratory distress (shown with bar graphs with diagonal fill lines) for the first-seventh markers 1105-1135. Graph 1300 also provides an indication of a range of error for each type of breathing in the form of an error bar. In this instance, the error bar represents a 95% confidence interval.

In step 1030, it may be determined whether the patient is in respiratory distress (i.e., has breathing similar to the restricted breathing) and an indication of whether the patient is in respiratory distress may be provided to a user such as a clinician, doctor, or nurse (step 1035).

A recently proposed treatment algorithm for patients with hypoxia due to COVID-19 suggests monitoring for signs including TAA when considering escalation of respiratory support from HFNC therapies to mechanical ventilation. This is because some patients whose respiratory rate and thoracoabdominal asynchrony are not rapidly relieved with HFNC are potentially at high risk of HFNC failure. Multiple studies suggest that while HFNC and non-invasive ventilation (NIV) may be sufficient for the management of respiratory failure in COVID-19 when utilized early enough, but the data are far from conclusive—stronger, evidence-based indications for selecting among forms NIV and selecting between NIV and invasive ventilation are needed.

Figure 14:
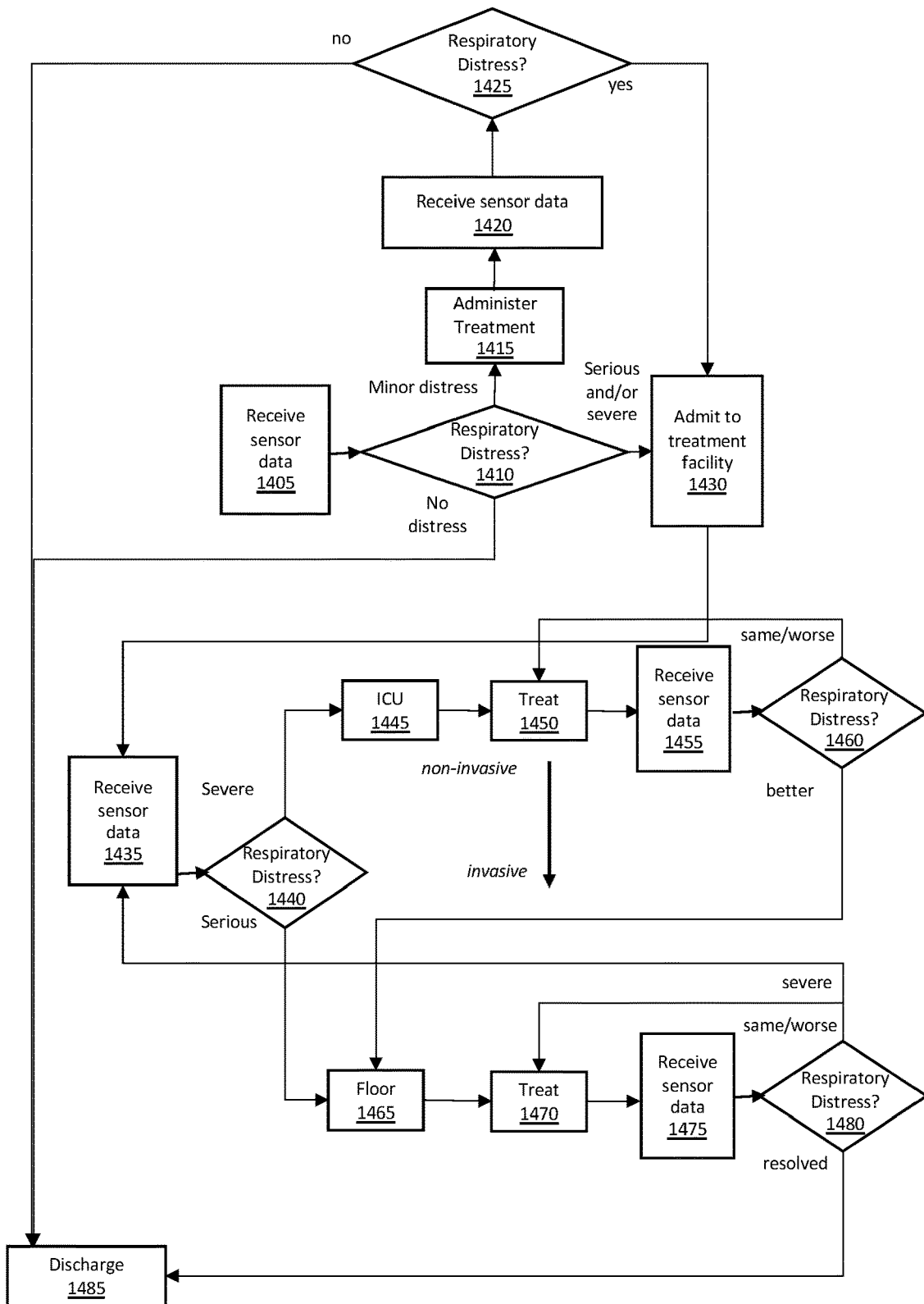
FIG. 14 is a flowchart showing exemplary steps of a process for treating a patient in respiratory distress, in accordance with embodiments of the present invention.

FIG. 14 is a flowchart showing exemplary steps of a process 1400 for treating a patient in respiratory distress using, for example, system 300 and/or components thereof, such as sensor array 310.

In step 1405, a set of sensor data for a patient may be received. The sensor data may be similar to the sensor data received in step 605 as explained above with regard to FIG. 6. In some embodiments, the first and second sets of data are from different sensors positioned on different portions of the patient's body (e.g., chest and abdomen or xiphoid process and abdomen). In some embodiments, the sensor data may be received when the patient arrives at a treatment facility (e.g., hospital for urgent care center) and/or when the patient is monitored at home for respiratory distress. Prior to step 1405, a sensor array, such as sensor array 310 may be placed on the patient's chest, xiphoid process, and abdomen so that data regarding how the chest, xiphoid process, and abdomen are moving when the patient is breathing. In step 1410, a determination of whether the patient is experiencing respiratory distress may be made by, for example, executing process 600, or portions thereof. An indication of the determination of step 1410 may then be provided to a clinician or caregiver for the patient. For the purposes of discussion of process 1400, the range of respiratory distress determinations are none, minor, moderate, or severe distress but it will be understood by those in the art that the indication of respiratory distress may be made and provided to a clinician in any appropriate formation (e.g., a numerical score or a graphic).

When the patient is not experiencing respiratory distress, he or she may be discharged from the treatment facility (step 1485). When it is determined that the patient is experiencing minor respiratory distress, a treatment such as albuterol may be administered (step 1415) and the patient may continue to be monitored to determine if the treatment is effective. In step 1420, another set of sensor data may be received, and it may be determined whether the patient is still in respiratory distress following treatment (step 1425). If the patient is no longer in respiratory distress, or if the respiratory distress is considered manageable in an out-patient setting as may be the case with a patient who is in recovery from a respiratory disease and/or a chronically-ill patient with, for example, chronic obstructive pulmonary disease (COPD), he or she may be discharged from the treatment facility (step 1485). When the patient is still in respiratory distress, he or she may be admitted to the treatment facility (e.g., hospital) for further treatment of his or her respiratory distress (step 1430).

When it is determined in step 1410, that the patient's respiratory distress is severe, the patient may be admitted to the treatment facility (e.g., hospital) for further treatment of his or her respiratory distress (step 1430). Upon admission to the treatment facility via the determination of 1410 or 1425, additional sensor data may be received (step 1435) so that a level of respiratory distress may be determined (step 1440) and a determination of whether to place the patient in the intensive care unit (severe respiratory distress) or on the floor of the hospital (moderate) may be made using the respiratory distress determination of step 1440. In some embodiments, step 1435 and 1440 may not be performed and the determination of whether to place the patient in the intensive care unit or on the floor of the hospital may be made using the respiratory distress determinations of steps 1410 or step 1425.

In step 1445, the patient may be placed in an intensive care unit (ICU) for further treatment (step 1450) with, for example, albuterol, HFNC, NIPPV, IPPV, and/or sedation and ventilation depending on the severity of respiratory distress and the patient's responsiveness to treatment. In order to determine the patient's responsiveness to treatment, the patient may be monitored, and an additional set of sensor data may be received (step 1455) on a continuous, periodic, and/or as-needed basis. The sensor data received in step 1455 may be used to determine whether there have been changes in the patient's respiratory distress (step 1460). When the patient's respiratory condition does not improve, or worsens, step 1450 may be repeated with progressively more aggressive and invasive treatment. When the patient's respiratory condition improves and/or when the respiratory distress of the patient is moderate, rather than severe, the patient may be moved to the treatment facility/hospital floor (step 1465) where he or she may receive a treatment (1470) such as albuterol, oxygen gas, and/or HFNC. While on the treatment facility/hospital floor, the patient may be monitored and sensor data may be received (step 1475) on a continuous, periodic, and/or as-needed basis and, when the respiratory distress is resolved, the patient may be discharged from the treatment facility. If the patient's respiratory distress is not resolved (e.g., the respiratory distress is the same or worse than a previously determined respiratory distress indicator), then treatment 1470 may continue and, when the patient's respiratory distress worsens to the point of being severe, he or she may be transferred to the intensive care unit (step 1445) and/or step 1435 may be repeated.

In some embodiments, when a patient is being monitored for respiratory distress using process 1400, a sensor array like sensor array 310 may be placed on the patient as shown in FIG. 4C prior to step 1405 and the patient may continuously wear the sensor array for a period of time when he or she is under treatment at the treatment facility. In this way, consistency of measurements may be achieved over time because different sensors and/or different sensor placements are not impacting any determination of respiratory distress. Additionally, or alternatively, the determinations regarding whether the patient is in respiratory distress of steps 1410, 1425, 1440, 1460, and/or 1480 may be made using process 600 so that the output is a respiratory distress severity score and/or an indication of a degree of severity for TAA for the patient.

In one use case, the processes described herein may be used in the assessment and management of acute infantile bronchiolitis, the most common cause of hospital admission in the first year of life. At present, the current standard for monitoring infants admitted to, for example, a hospital for bronchiolitis, is administration of a series of regular and repeated assessments of the infant by trained clinicians as well as the monitoring of respiratory rate, oxygen saturation, and signs of increased work of breathing, including thoracoabdominal asynchrony, nasal flaring, and accessory muscle use, among others. Oftentimes, the infant must be continuously monitored to detect respiratory deterioration that would otherwise go undetected with intermittent clinical assessment and thus progress to more severe disease. This continuous monitoring by trained clinical staff is laborious and expensive in terms of cost and use of resources (e.g., the clinical staff). Further, direct observation and assessment of the infant is subject to errors caused by, for example, inter-observability and relativistic assessments (as opposed to an absolute diagnosis or assessment).

The spectrum of oxygen and ventilatory support utilized in the treatment of bronchiolitis, from least to most invasive, spans from supplemental oxygen (via nasal cannula or face mask) to high flow nasal cannula (HFNC) to continuous positive airway pressure (CPAP) to invasive mechanical ventilation in the most severe cases. Monitoring of breathing effort via the systems and processes described herein would provide clinicians the ability to continuously monitor a patient with bronchiolitis without the need for continuous and direct observation and assessment of the patient. This has several advantages when compared with the current standard of care including, but not limited to, the ability to passively, continuously, and consistently monitor the effort the patient exerts while breathing so that changes (improvements or declines) may be accurately measured over time and treatment plans may be adjusted accordingly. For example, information provided by the systems and processes described herein (e.g., respiratory distress severity score, degree of effort to breathe, etc.) may assist a clinician when making decisions regarding a severity of the patient's condition or respiratory distress and/or decisions regarding the escalation and de-escalation of respiratory and/or ventilatory support in this context.

In a prototypical use case in the management and/or treatment of bronchiolitis, a patient with symptoms of respiratory distress presents to a treatment facility (e.g., urgent care clinic, hospital, emergency department of a hospital) where array 310 may be placed on a patient so that sensor data may be received (step 1405 of process 1400). When the degree of respiratory distress is minor (or inconclusive) (step 1410), treatment in the form of, for example, supplemental oxygen may be administered (step 1415). Sensor data may again be received (step 1420) and if the patient is still in respiratory distress (step 1425), he or she may be admitted to the general hospital ward (e.g., step 1430) for suspected bronchiolitis. Alternatively, a patient may be directly admitted to the general hospital ward if the patient is observed to have overt respiratory distress when entering the treatment facility (i.e., process 1400 may start at step 1415 (e.g., when sensor data is not gathered because respiratory distress is readily observable) and/or process 1400 may start at step 1430). The patient may be continuously monitored (step 1425 and 1440) for respiratory distress via, for example, execution of process 600. If serious respiratory distress is detected and/or if there is moderate respiratory decline, an alarm may be issued alerting the care team of the patient's condition. A clinician may then observe the patient to assess his or her condition and, if necessary, treatment provided to the patient may be adjusted (step 1450 or 1470) (e.g., oxygen requirements of the patient and/or escalation of respiratory therapy (e.g., escalation to non-invasive ventilation such as CPAP)). Intensive Care Unit admission may occur at this stage and continuous monitoring of the patient with the systems described herein may continue (steps 1445-1460).

Should the clinical team then receive an alarm from the systems described herein indicating severe respiratory distress and/or decline (step 1440 or 1460), mechanical ventilation may be considered, especially in setting of other indications for intubation such as poor mental status, severe hypoxemia, or hypercapnia. Alternatively, should the system indicate an improvement in respiratory status (e.g., step 1460), the patient could be weaned from oxygen support therapy and potentially transferred from the ICU to the floor of the hospital (step 1465). The patient could then continue to be monitored (steps 1475-1480) until discharge, which would only occur once the sensor data, as well as physical examination, indicate minimal work of breathing in the absence of supportive therapy. This would translate to a near normal score of respiratory severity.

In another use case, the systems, devices, and processes described herein may be used in the diagnosis and management (or treatment) of COVID-19 (or non-COVID-19) acute respiratory distress syndrome ARDS. At present, there is conflicting evidence regarding the role of high-flow nasal cannula (HFNC) and non-invasive ventilation (NIV) in the early management of COVID-19 respiratory distress. Some studies have found no evidence of increased mortality after delaying intubation in favor of HFNC or NIV, suggesting that in less severe disease, such modalities can be used to successfully treat the disease while avoiding the potential for injuries associated with invasive ventilation. Other studies have found that failure to intubate early leads to increased mortality, owing to rapid deterioration and patient self-induced lung injury (P-SILI) due to overly vigorous spontaneous ventilation. When these factors are considered with the risk of aerosolization of the virus with HFNC and NIV, thereby exposing bedside healthcare providers, early intubation may be considered a preferred approach for the management of a respiratory disease or infection like SARS, MERS, SARS-CoV-2 (i.e., COVID-19) respiratory distress. Continuous monitoring of breathing effort using the systems, devices, and processes described herein may provide valuable indications of respiratory distress and/or a degree of effort the patient exerts to breathe, which may help guide early oxygen enrichment therapy and intubation strategy in patients with COVID-19. In this use case, a system and/or device as described herein may be placed upon a patient with either suspected or confirmed respiratory infection who is exhibiting observable signs of moderate respiratory distress, increased work of breathing by physical examination, and/or hypoxemia upon hospital admission (step 1430 which may be performed with, or without, the sensor data received at step(s) 1405 and/or 1420). In the absence of significant dyspnea or severe respiratory distress (step 1440), the patient may initially be treated with a brief (less than 24 hour) HFNC or non-invasive ventilation (NIV) (step 1470) while being monitored (continuously, periodically, and/or as-needed) with the systems/devices described herein in order to determine a degree of effort the patient is exerting while breathing, a degree of respiratory distress, and/or a respiratory distress score over time (step 1480). The systems and/or devices described herein may be used to determine the success of the NIV trial (step 1480) via, for example, comparing respiratory distress scores and/or respiratory effort determinations over time to quantify improvement or further decline. If the patient's condition stabilizes and/or improves (e.g., improving respiratory distress scores or decreased effort to breathe) treatment may be continued and/or de-escalated. If the patient's condition declines and/or when further decompensation is indicated, escalation to more aggressive and/or invasive treatment (e.g., mechanical ventilation) and/or admission to the ICU (step 1480) may be warranted.

A standard of care is to begin the process of weaning a patient from mechanical ventilation as soon as 24-hours after intubation provided that the patient can breathe at least somewhat on his or her own. Ventilator modes that allow for spontaneous breathing, whether assisted or unassisted, may facilitate this process. However, weaning a patient from a ventilator poses dangers/risks to the patient as may occur when high respiratory efforts lead to uncontrolled transpulmonary pressures and leave the patient at risk of P-SILI and weaning failure. The described system can be used to ensure adequately minimized efforts during spontaneous breathing in mechanical ventilation by monitoring the effort the patient is exerting while breathing so that adequate adjustments and/or countermeasures may be taken with, for example, ventilation equipment to reduce risks to the patient. For example, if the patient's breathing effort is determined to be higher than desired (e.g., a respiratory effort score that is above a desired value or threshold) by the clinical care team, the ventilator mode may be adjusted to controlled ventilation, where the patient's respiration is completely controlled by the ventilator, which may serve to decrease the amount of effort the patient is exerting while breathing. On the other hand, there is increasing evidence that insufficient patient effort during mechanical ventilation has been associated with atrophic diaphragm injury due to muscle inactivity. For this reason, the system can also be used to ensure adequately elevated breathing efforts (e.g., a respiratory effort score that is above a desired value or threshold) by the patient are being exerted. If the effort the patient is exerting to breathe is insufficient (a respiratory effort score that is below a desired value or threshold), in response to this insufficient effort, a care team can adjust ventilator settings to allow for greater spontaneous breathing and less assisted breaths.

We claim:

1. A method comprising:
    receiving, by a processor, a first set of sensor data from a first sensor positioned on the epidermis of a patient being monitored for respiratory distress syndrome in a first location, the first sensor being in communication with the processor;
    receiving, by the processor, a second set of sensor data from a second sensor positioned on the epidermis of the patient in a second location, the second sensor being in communication with the processor;
    determining, by the processor, a phase difference between the first and second sets of sensor data;

determining, by the processor, a degree of respiratory effort exhibited by the patient over a time period based on a determined phase difference between the first and second sets of sensor data;

determining, by the processor, a change in the patient's respiratory distress syndrome over the time period responsively to the determined degree of respiratory effort exhibited by the patient over the time period; and communicating, by the processor, the change in the patient's respiratory distress syndrome to a display device.

2. The method of claim 1, wherein the determination of the degree of respiratory effort exhibited by the patient includes determining a degree of thoraco-abdominal asynchrony (TAA) exhibited by the patient.

3. The method of claim 1, wherein the first and second sensors are accelerometers and the first and second sets of sensor data include acceleration measurements.

4. The method of claim 1, wherein the first and second sensors are force meters and the first and second sets of sensor data include force measurements.

5. The method of claim 1, wherein the first and second sensors are strain sensors and the first and second sets of sensor data include strain measurements.

6. The method of claim 1, further comprising:
receiving an indication of a respiratory rate of the patient, wherein the determination of the degree of respiratory effort exhibited by the patient is further based on the respiratory rate.

7. The method of claim 1, further comprising:
receiving a third set of sensor data from a third sensor positioned on the epidermis of the patient in a third location, the third sensor being in communication with the processor;
determining a phase difference between at least one of the first and third sets of sensor data and the second and third sets of sensor data, wherein determining the degree of respiratory effort exhibited by the patient is further based on a determined phase difference between the first and third sets of sensor data and the second and third sets of sensor data.

8. The method of claim 1, further comprising:
performing, by the processor, cross-correlation analysis between the first and second sets of sensor data prior to determining the degree of respiratory effort exhibited by the patient, wherein the degree of respiratory effort exhibited by the patient is further based on a result of the cross-correlation analysis.

9. The method of claim 8, wherein the first and second sets of sensor data are a signal collected over the time period, the method further comprising:
mapping a result of a cross-correlation calculation at a particular time during the time period with a maximum cross-correlation value calculated during the time period prior to the determination of the degree of respiratory effort exhibited by the patient.

10. The method of claim 1, further comprising:
receiving an indication of a respiratory rate variability of the patient, wherein the determination of the degree of respiratory effort exhibited by the patient is further based on respiratory rate variability.

11. A method comprising:
receiving, by a processor, a first set of sensor data from a first sensor positioned on the epidermis of a patient being monitored for respiratory distress syndrome in a first location, the first sensor being in communication with the processor;

receiving, by the processor, a second set of sensor data from a second sensor positioned on the epidermis of the patient in a second location, the second sensor being in communication with the processor;

performing, by the processor, cross-correlation analysis between the first and second sets of sensor data;

determining, by the processor, a degree of respiratory effort exhibited by the patient over a time period based on a result of the cross-correlation analysis;

determining, by the processor, a change in the patient's respiratory distress syndrome over the time period responsively to the determined degree of respiratory effort exhibited by the patient over the time period; and communicating, by the processor, the change in the patient's respiratory distress syndrome to a display device.

12. The method of claim 11, wherein the determination of the degree of respiratory effort exhibited by the patient includes determining a degree of thoraco-abdominal asynchrony (TAA) exhibited by the patient.

13. The method of claim 11, wherein the first and second sensors are accelerometers and the first and second sets of sensor data include acceleration measurements.

14. The method of claim 11, wherein the first and second sensors are force meters and the first and second sets of sensor data include force measurements.

15. The method of claim 11, wherein the first and second sensors are strain sensors and the first and second sets of sensor data include strain measurements.

16. The method of claim 11, further comprising:
receiving an indication of a respiratory rate of the patient, wherein the determination of the degree of respiratory effort exhibited by the patient is further based on the respiratory rate.

17. The method of claim 11, further comprising:
determining, by the processor, a phase difference between the first and second sets of sensor data prior to determining the degree of respiratory effort exhibited by the patient, wherein the degree of respiratory effort exhibited by the patient is further based on a determined phase difference.

18. The method of claim 17, wherein the first and second sets of sensor data are a signal collected over the time period, the method further comprising:
mapping a result of a cross-correlation calculation at a particular time during the time period with a maximum cross-correlation value calculated during the time period prior to the determination of the degree of respiratory effort exhibited by the patient.

19. The method of claim 11, further comprising:
receiving a third set of sensor data from the third sensor positioned on the epidermis of the patient in a third location, the third sensor being in communication with the processor;
performing, by the processor, cross-correlation analysis between the first and third sets of data or the second and third sets of sensor data, wherein determining the degree of respiratory effort exhibited by the patient is further based on a result of the cross-correlation analysis between the first and third sets of sensor data or the second and third sets of sensor data.

20. The method of claim 11, further comprising:
receiving an indication of a respiratory rate variability of the patient, wherein the determination of the degree of respiratory effort exhibited by the patient is further based on respiratory rate variability.

\* \* \* \* \*